(12) United States Patent
Seiler et al.

(10) Patent No.: US 7,413,579 B2
(45) Date of Patent: Aug. 19, 2008

(54) METHOD FOR DYEING FIBERS CONTAINING KERATIN

(75) Inventors: Martina Seiler, Duisburg (DE); Detlef Hollenberg, Erkrath (DE)

(73) Assignee: Henkel Kommanditgesellschaft auf Aktien, Dusseldorf (DE)

( * ) Notice: Subject to any disclaimer, the term of this patent is extended or adjusted under 35 U.S.C. 154(b) by 0 days.

(21) Appl. No.: 11/438,514

(22) Filed: May 22, 2006

(65) Prior Publication Data
US 2006/0265818 A1    Nov. 30, 2006

Related U.S. Application Data

(63) Continuation of application No. PCT/EP2004/010510, filed on Sep. 18, 2004.

(30) Foreign Application Priority Data
Nov. 21, 2003    (DE) ................. 103 54 812

(51) Int. Cl.
*A61Q 5/10* (2006.01)
(52) U.S. Cl. ............... 8/405; 8/406; 8/410; 8/411; 8/412; 8/435; 8/485; 132/202; 132/208; 424/70.6
(58) Field of Classification Search .......... 8/405, 8/406, 410, 411, 412, 435, 485; 132/202, 132/208; 424/70.6
See application file for complete search history.

(56) References Cited
U.S. PATENT DOCUMENTS

| 4,931,218 A | 6/1990 | Schenker |
| 5,061,289 A | 10/1991 | Clausen et al. |
| 5,294,726 A | 3/1994 | Behler et al. |

(Continued)

FOREIGN PATENT DOCUMENTS

DE    2359399    12/1975

(Continued)

OTHER PUBLICATIONS

K. Schrader, Gundlagen und Rezepturen der Kosmetika. 2. Auflage, ( ), (1989).

(Continued)

*Primary Examiner*—Eisa B Elhilo
(74) *Attorney, Agent, or Firm*—John E. Drach

(57) ABSTRACT

A method for dyeing keratin-containing fibers, in particular, human hair comprising the steps of: (A) contacting the hair with a dyeing composition, comprising color-imparting components for a contact time Z1; (B) rinsing the hair a to remove the dying composition; (C) optionally drying the rinsed hair; (D) contacting at least a portion of the hair from step (B) or (C) with a lightening or nuancing agent comprising, in a cosmetic carrier, at least one thickener, hydrogen peroxide and at least one alkalinizing agent for a contact time Z2; and (E) rinsing the hair to remove the adjusting agent; wherein the dyeing composition comprises a color-imparting component comprising, (a) at least two oxidation dye precursors, where at least one oxidation dye precursor must be of the developer type or
(b) at least two oxo dye precursors, where at least one oxo dye precursor must be a reactive carbonyl compound.

The method ensures a uniform lightening of keratin-containing fibers dyed with dyeing compositions, and produces uniform and natural-looking, lightened color reflections over the entire head hair area.

13 Claims, 4 Drawing Sheets

U.S. PATENT DOCUMENTS

| | | |
|---|---|---|
| 5,380,340 A | 1/1995 | Neunhoeffer et al. |
| 5,534,267 A | 7/1996 | Neunhoeffer et al. |
| 5,766,576 A | 6/1998 | Loewe et al. |
| 6,099,592 A | 8/2000 | Vidal et al. |
| 6,284,003 B1 | 9/2001 | Rose et al. |
| 6,371,993 B1 | 4/2002 | Moeller et al. |
| 6,719,811 B1 | 4/2004 | Konrad et al. |
| 6,790,239 B1 | 9/2004 | Moeller et al. |
| 2003/0154562 A1* | 8/2003 | Sarojini et al. ............... 8/405 |
| 2005/0097684 A1* | 5/2005 | Narasimhan et al. .......... 8/405 |

FOREIGN PATENT DOCUMENTS

| | | |
|---|---|---|
| DE | 3723354 | 1/1989 |
| DE | 3725030 | 2/1989 |
| DE | 3843892 | 6/1990 |
| DE | 3926344 | 2/1991 |
| DE | 4133957 | 4/1993 |
| DE | 19543988 | 5/1997 |
| DE | 29908573 | 5/1999 |
| DE | 19721785 | 10/2001 |
| DE | 10037580 | 2/2002 |
| EP | 0530229 | 3/1993 |
| EP | 0740931 | 11/1996 |
| EP | 0998908 | 5/2000 |
| GB | 1026978 | 4/1966 |
| GB | 1153196 | 5/1969 |
| JP | 02019576 | 1/1990 |
| WO | WO9408969 | 4/1994 |
| WO | WO9408970 | 4/1994 |
| WO | WO9615765 | 5/1996 |
| WO | WO9918916 | 4/1999 |
| WO | WO0038638 | 7/2000 |
| WO | WO00134106 | 5/2001 |
| WO | WO0147483 | 7/2001 |
| WO | WO0176546 | 10/2001 |
| WO | WO03082236 | 10/2003 |

OTHER PUBLICATIONS

C. Zviak, The Science of Hair Care, Chapter 7 (pp. 248-250) Chapter 8 (pp. 264-267) vol. 7 of the Dermatology Series Marcel Dekker Inc. New York, Basel, (1986).

* cited by examiner

METHOD FOR DYEING FIBERS CONTAINING KERATIN

CROSS-REFERENCE TO RELATED APPLICATIONS

This application is a continuation under 35 U.S.C. § 365(c) and 35 U.S.C. § 120 of International Application PCT/EP2004/010510, filed Sep. 18, 2004. This application also claims priority under 35 U.S.C. § 119 of German Application DE 103 54 812.2, filed Nov. 21, 2003. Each of the applications is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to a method for dyeing keratin-containing fibers, in particular, human hair, in which, after a dyeing step, some of the previously dyed fibers are selectively subjected to incomplete, oxidative color removal for the nuancing. In addition, the invention provides a kit-of-parts comprising a dyeing composition and a color removal agent, and application aids, and the use of this kit in the dyeing method according to the invention.

Human hair is nowadays treated in diverse ways with hair cosmetic preparations. These include, for example, the cleansing of the hair with shampoos, the care and regeneration with rinses and treatments, and the bleaching, dyeing and shaping of the hair with dyeing compositions, tinting compositions, waving compositions and styling preparations. In this respect, compositions for changing or nuancing the color of head hair play a prominent role. Disregarding the bleaching compositions which bring about an oxidative lightening of the hair by breaking down the natural hair dyes, then in the field of hair dyeing essentially four types of hair dyeing compositions are of importance.

For permanent, intense colorations with corresponding fastness properties, so-called oxidation dyeing compositions are used. Such dyeing compositions usually comprise oxidation dye precursors, so-called developer components and coupler components. The developer components form the actual dyes under the influence of oxidizing agents or of atmospheric oxygen with one another or with coupling with one or more coupler components. The oxidation dyeing compositions are indeed notable for excellent, long-lasting coloring results. However, for colorations which appear natural, it is usually necessary to use a mixture of a relatively large number of oxidation dye precursors; in many cases, in addition, direct dyes are used for the nuancing.

The developer components used are usually primary aromatic amines with a further free or substituted hydroxy or amino group located in the para or ortho position, diaminopyridine derivatives, heterocyclic hydrazones, 4-aminopyrazolone derivatives and 2,4,5,6-tetraminopyrimidine and derivatives thereof.

Specific representatives are, for example, p-phenylenediamine, p-tolylenediamine, 2,4,5,6-tetraminopyrimidine, p-aminophenol, N,N-bis(2-hydroxyethyl)-p-phenylenediamine, 2-(2,5-diaminophenyl)ethanol, 2-(2,5-diaminophenoxy)ethanol, 1-phenyl-3-carboxyamido-4-aminopyrazolone-5,4-amino-3-methylphenol, 2-aminomethyl-4-aminophenol, 2-hydroxy-4,5,6-triaminopyrimidine, 2,4-dihydroxy-5,6-diaminopyrimidine, 2,5,6-triamino-4-hydroxypyrimidine and 1,3-N,N'-bis(2-hydroxyethyl)-N,N'-bis(4-aminophenyl)diaminopropan-2-ol.

The coupler components used are generally m-phenylenediamine derivatives, naphthols, resorcinol and resorcinol derivatives, pyrazolones and m-aminophenols. Suitable coupler substances are, in particular, 1-naphthol, 1,5-dihydroxynaphthalene, 2,7-dihydroxynaphthalene and 1,7-dihydroxynaphthalene, 5-amino-2-methylphenol, m-aminophenol, resorcinol, resorcinol monomethyl ether, m-phenylenediamine, 1-phenyl-3-methylpyrazolone-5, 2,4-dichloro-3-aminophenol, 1,3-bis(2,4-diaminophenoxy)propane, 2-chlororesorcinol, 4-chlororesorcinol, 2-chloro-6-methyl-3-aminophenol, 2-methylresorcinol, 5-methylresorcinol and 2-methyl-4-chloro-5-aminophenol.

For temporary colorations, use is usually made of dyeing or tinting compositions which comprise so-called direct dyes as coloring component. These are dye molecules which attach directly to the hair and require no oxidative process for color formation. These dyes include, for example, henna, which is known for coloring bodies and hair since antiquity. These colorations are generally considerably more sensitive to shampooing than the oxidative colorations, meaning that an often undesired nuance shift or even a visible "decoloring" takes place very much more quickly.

(2) Description of Related Art, Including Information Disclosed Under 37 C.F.R. §§ 1.97 and 1.98

Finally, a further dyeing method has received great attention. In this method, precursors of the natural hair dye melanine are applied to the hair; in the course of oxidative processes within the hair, these then form nature-analogous dyes. Such a method using 5,6-dihydroxyindoline as dye precursor has been described in EP-B1-530 229. Upon, in particular, repeated, application of compositions comprising 5,6-dihydroxyindoline it is possible to give back the natural hair color to people with gray hair. The color formation here can take place with atmospheric oxygen as the sole oxidizing agent, meaning that it is not necessary to have recourse to any further oxidizing agents. For people with originally mid-blonde to brown hair, the indoline can be used as the sole dye precursor. For application on people with originally red and, in particular, dark to black hair color, by contrast, satisfactory results can often only be achieved through the co-use of further dye components, in particular, specific oxidation dye precursors.

Another way of dyeing keratin-containing fibers is to use dyeing compositions which comprise a combination of component A compounds which comprise a reactive carbonyl group with component B compounds chosen from (a) CH-acidic compounds, (b) compounds with primary or secondary amino group or hydroxy group chosen from primary or secondary aromatic amines, nitrogen-containing heterocyclic compounds and aromatic hydroxy compounds, (c) amino acids, (d) oligopeptides constructed from 2 to 9 amino acids.

The corresponding dyeing method (called oxo dyeing below) is described, for example, in the publications WO-A1-99/18916, WO-A1-00/38638, WO-A1-01/34106 and WO-A1-01/47483. Some of the resulting colorations have color fastnesses on the keratin-containing fibers which are comparable to those of oxidation dyeing. The nuance spectrum which can be achieved with the gentle oxo dyeing is very broad and the coloration obtained often has an acceptable brilliance and depth of color. The above-mentioned components A and B, referred to below as oxo dye precursors, are generally themselves not dyes, and therefore when taken by themselves are not suitable for dyeing keratin-containing fibers. In combination, they form dyes in a nonoxidative process. Among compounds of component B, however, corresponding oxidation dye precursors of the developer and/or coupler type can also be used with or without the use of an oxidizing agent. Thus, the method of oxo dyeing can be readily combined with the oxidative dyeing system.

Methods are known to the person skilled in the art in which the hair is lightened or bleached on selective areas through the application of so-called bleaching agents. The result of these methods, e.g., on undyed hair which has been left natural are, for example, blonde strands or lightened hair ends.

The oxidizing agents present in the bleaching compositions have an oxidizing effect on the natural hair dye melanin and optionally on synthetic dyes located in the fiber and thereby cause a color change and optimally lightening of the hair color. The principles of bleaching processes and oxidative dyeing processes are known to the person skilled in the art and are summarized in relevant monographs, e.g., by K. Schrader, Grundlagen und Rezepturen der Kosmetika [Principles and formulations of cosmetics], $2^{nd}$ edition, 1989, Dr. Alfred Hüthig Verlag, Heidelberg, or W. Umbach (ed.), Kosmetik (cosmetics), $2^{nd}$ edition, 1995, Georg Thieme Verlag, Stuttgart, N.Y.

For the lightening or ultrableaching of human hair—particularly for strand application—solid or paste-like preparations comprising solid oxidizing agents are usually mixed directly prior to application with a dilute hydrogen peroxide solution. This application mixture is then applied to the hair and rinsed out again after a certain contact time. Besides hydrogen peroxide, the conventional ready-to-use bleaching compositions for keratin-containing fibers in most cases comprise peroxydisulfate compounds for increasing the lightening capacity and, upon application to the fibers, have a pH greater than pH 9. However, the result of a lightening operation should be differentiated from the result of the ultrableaching. Whereas during the ultrableaching operation as far as possible all of the color pigments are oxidatively influenced with retention of a virtually white-colored hair fiber, in the case of oxidative lightening, the existing coloration should be nuanced (i.e., lightened) in such a way that the starting color is still recognizable, but appears lighter in color to the observer.

However, the desired oxidative lightening of keratin-containing fibers treated with dyeing compositions cannot be effected directly. Often, the oxidative lightening of such color-changed fibers results in undesired color shifts to, e.g., orange or green tones, which unquestionably have to be avoided. In the course of lightening, the only color effects which are desirable are those which signify a lightening of the starting shade. In addition, it is desirable to uniformly nuance a well-defined part of the head hair, such as, for example, strands and to distribute these well-defined parts again as uniformly as possible over the entire head hair area. For strand nuancing, this means that a hair fiber has to be nuanced uniformly from the roots of the hair to the ends and these strands should settle as evenly distributed as possible both in the covering hair and also in the areas of hair which are underneath. In this way, uniform and natural-looking, lightened color reflections are obtained.

BRIEF SUMMARY OF THE INVENTION

An object of the present invention is therefore to provide a method which ensures a uniform lightening of keratin-containing fibers dyed with dyeing compositions, and produces uniform and natural-looking, lightened color reflections over the entire head hair area.

Surprisingly, it has been found that uniform color reflections can be achieved without undesired color shifts during oxidative lightening if the oxidative lightening takes place after the dyeing step, the dyeing composition comprises a defined minimum number of color-imparting components and a lightening agent, called nuancing agent below, with a defined viscosity is used.

One aspect of the present invention pertains to a method for dyeing keratin-containing fibers, in particular, human hair, comprising the steps of: (A) contacting the hair with a dyeing composition, comprising color-imparting components for a contact time Z1; (B) rinsing the hair to remove the dying composition; (C) optionally drying the rinsed hair; (D) contacting at least a portion of the hair from step (B) or (C) with a nuancing agent comprising, in a cosmetic carrier, at least one thickener, hydrogen peroxide and at least one alkalinizing agent for a contact time Z2; (E) rinsing the hair to remove the adjusting agent; wherein the dyeing composition comprises a color-imparting component comprising,
  (a) at least two oxidation dye precursors, where at least one oxidation dye precursor must be of the developer type or
  (b) at least two oxo dye precursors, where at least one oxo dye precursor must be a reactive carbonyl compound.

Another aspect of the invention pertains to a kit comprising
  optionally an applicator,
  a container C1 comprising a dyeing composition,
  a container C2a comprising a composition comprising hydrogen peroxide and
  a container C2b comprising a composition comprising at least one thickener and at least one alkalinizing agent, where the dyeing composition comprises, as color-imparting component,
  (a) at least two oxidation dye precursors, where at least one oxidation dye precursor must be of the developer type or
  (b) at least two oxo dye precursors, where at least one oxo dye precursor must be a reactive carbonyl compound.

DETAILED DESCRIPTION OF THE INVENTION

Figure 1:
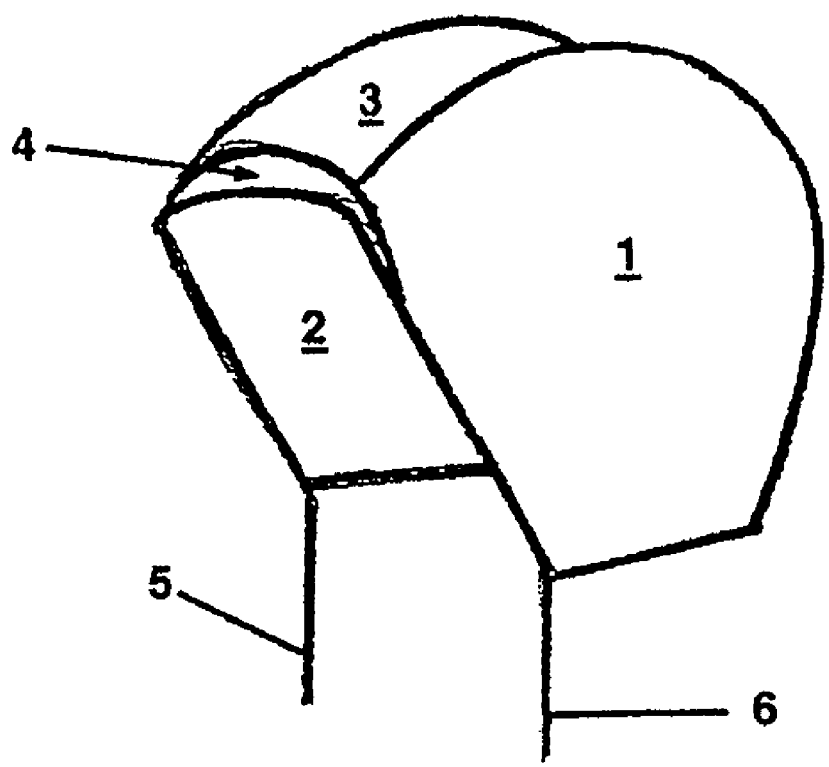
FIG. 1. Depicts a partial side view of a cap according to the invention.

For the purposes of this application, keratin-containing fibers are understood as meaning furs, wool, feathers and, in particular, human hair. Although the dyeing compositions of the method according to the invention are primarily suitable for dyeing keratin fibers, nothing in principle precludes a use also in other areas, in particular, in color photography.

After carrying out the method according to the invention, color pairs are produced which are formed from a starting coloration and the subsequent nuancing through the lightening after step C of the method according to the invention. According to the invention, the starting coloration is defined as the coloration of the fibers obtained after step A. The lightening produces a lightened coloration in the nuance of the starting coloration. The formation of such color pairs according to the invention can be determined using colorimetry.

If the dyeing composition of the method according to the invention is an oxidative dyeing composition, it comprises at least one developer component. The developer components used are usually primary aromatic amines with a further free or substituted hydroxy or amino group located in the para or ortho position, diaminopyridine derivatives, heterocyclic hydrazones, 4-aminopyrazole derivatives and 2,4,5,6-tetraminopyrimidine and derivatives thereof.

According to the invention, it may be preferred to use a p-phenylenediamine derivative or one of its physiologically compatible salts as developer component. Particular preference is given to p-phenylenediamine derivatives of the formula (E1)

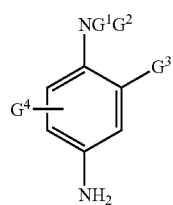

(E1)

where

G$^1$ is a hydrogen atom, a C$_1$- to C$_4$-alkyl radical, a C$_1$- to C$_4$-monohydroxyalkyl radical, a C$_2$- to C$_4$-polyhydroxyalkyl radical, a (C$_1$- to C$_4$)-alkoxy(C$_1$- to C$_4$)-alkyl radical, a 4'-aminophenyl radical or a C$_1$- to C$_4$-alkyl radical which is substituted by a nitrogen-containing group, a phenyl radical or a 4'-aminophenyl radical;

G$^2$ is a hydrogen atom, a C$_1$- to C$_4$-alkyl radical, a C$_1$- to C$_4$-monohydroxyalkyl radical, a C$_2$- to C$_4$-polyhydroxyalkyl radical, a (C$_1$- to C$_4$)-alkoxy(C$_1$- to C$_4$)-alkyl radical or a C$_1$- to C$_4$-alkyl radical which is substituted by a nitrogen-containing group;

G$^3$ is a hydrogen atom, a halogen atom, such as a chlorine, bromine, iodine or fluorine atom, a C$_1$- to C$_4$-alkyl radical, a C$_1$- to C$_4$-monohydroxyalkyl radical, a C$_2$- to C$_4$-polyhydroxyalkyl radical, a C$_1$- to C$_4$-hydroxyalkoxy radical, a C$_1$- to C$_4$-acetylaminoalkoxy radical, a C$_1$- to C$_4$-mesylaminoalkoxy radical or a C$_1$- to C$_4$-carbamoylaminoalkoxy radical;

G$^4$ is a hydrogen atom, a halogen atom or a C$_1$- to C$_4$-alkyl radical or if G$^3$ and G$^4$ are in the ortho position relative to one another, they can together form a bridging α,ω-alkylenedioxo group, such as, for example, an ethylenedioxy group.

Examples of the C$_1$- to C$_4$-alkyl radicals specified as substituents in the compounds according to the invention are the groups methyl, ethyl, propyl, isopropyl and butyl. Ethyl and methyl are preferred alkyl radicals. C$_1$- to C$_4$-alkoxy radicals preferred according to the invention are, for example, a methoxy or an ethoxy group. Furthermore, preferred examples of a C$_1$- to C$_4$-hydroxyalkyl group which may be mentioned are a hydroxymethyl, a 2-hydroxyethyl, a 3-hydroxypropyl or a 4-hydroxybutyl group. A 2-hydroxyethyl group is particularly preferred. A particularly preferred C$_2$- to C$_4$-polyhydroxyalkyl group is the 1,2-dihydroxyethyl group. Examples of halogen atoms according to the invention are F, Cl or Br atoms, Cl atoms are very particularly preferred. The other terms used are derived according to the invention from the definitions given here. Examples of nitrogen-containing groups of the formula (E1) are, in particular, the amino groups. C$_1$- to C$_4$-monoalkylamino groups, C$_1$- to C$_4$-dialkylamino groups, C$_1$- to C$_4$-trialkylamino groups, C$_1$- to C$_4$-monohydroxyalkylamino groups, imidazolinium and ammonium.

Particularly preferred p-phenylenediamines of the formula (E1) are chosen from p-phenylenediamine, p-tolylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis(β-hydroxyethyl)-p-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl, β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine and 5,8-diaminobenzo-1,4-dioxane, and their physiologically compatible salts.

p-Phenylenediamine derivatives of the formula (E1) very particularly preferred according to the invention are p-phenylenediamine, p-tolylenediamine, 2-(β-hydroxyethyl)-p-phenylenediamine, 2-(α,β-dihydroxyethyl)-p-phenylenediamine and N,N-bis(β-hydroxyethyl)-p-phenylenediamine.

According to the invention, it may also be preferred to use as developer component compounds which comprise at least two aromatic nuclei which are substituted by amino and/or hydroxyl groups.

Among the binuclear developer components which can be used in the dyeing compositions according to the invention, mention may be made in particular, of the compounds which conform to the following formula (E2), and their physiologically compatible salts:

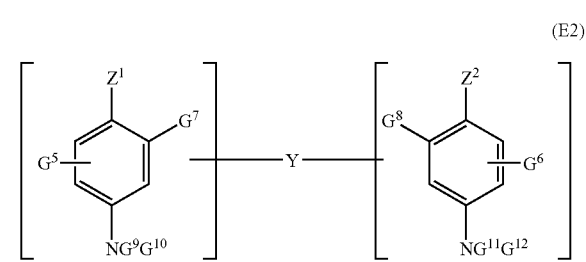

(E2)

where:

Z$^1$ and Z$^2$, independently of one another, are a hydroxyl or NH$_2$ radical, which is optionally substituted by a C$_1$- to C$_4$-alkyl radical, by a C$_1$- to C$_4$-hydroxyalkyl radical and/or by a bridge Y or which is optionally part of a bridging ring system, the bridge Y is an alkylene group having 1 to 14 carbon atoms, such as, for example, a linear or branched alkylene chain or an alkylene ring, which can be interrupted or terminated by one or more nitrogen-containing groups and/or one or more heteroatoms, such as oxygen, sulfur or nitrogen atoms and may possibly be substituted by one or more hydroxyl or $C_1$- to $C_8$-alkoxy radicals, or a direct bond, $G^5$ and $G^8$, independently of one another, are a hydrogen or halogen atom, a $C_1$- to $C_4$-alkyl radical, a $C_1$- to $C_4$-monohydroxyalkyl radical, a $C_2$- to $C_4$-polyhydroxyalkyl radical, a $C_1$- to $C_4$-aminoalkyl radical or a direct bond to the bridge Y, $G^7$, $G^8$, $G^9$, $G^{10}$, $G^{11}$ and $G^{12}$, independently of one another, are a hydrogen atom, a direct bond to the bridge Y or a $C_1$- to $C_4$-alkyl radical, with the provisos that the compounds of the formula (E2) comprise only one bridge Y per molecule and the compounds of the formula (E2) comprise at least one amino group which carries at least one hydrogen atom.

According to the invention, the substituents in formula (E2) are defined analogously to the above statements.

Preferred binuclear developer components of the formula (E2) are, in particular: N,N'-bis(β-hydroxyethyl)-N,N'-bis (4'-aminophenyl)-1,3-diaminopropan-2-ol, N,N'-bis(β-hydroxyethyl)-N,N'-bis(4'-aminophenyl)ethylenediamine, N,N'-bis(4-aminophenyl)tetramethylenediamine, N,N'-bis (β-hydroxyethyl)-N,N'-bis(4-aminophenyl)tetramethylenediamine, N,N'-bis(4-methylaminophenyl)tetramethylenediamine, N,N'-diethyl-N,N'-bis(4'-amino-3'-methylphenyl) ethylenediamine, bis(2-hydroxy-5-aminophenyl)methane, 1,3-bis(2,5-diaminophenoxy)propan-2-ol, N,N'-bis(4'-aminophenyl)-1,4-diazacycloheptane, N,N'-bis(2-hydroxy-5-aminobenzyl)piperazine, N-(4'-aminophenyl)-p-phenylenediamine and 1,10-bis(2',5'-diaminophenyl)-1,4,7,10-tetraoxadecane and their physiologically compatible salts.

Very particularly preferred binuclear developer components of the formula (E2) are N,N'-bis(β-hydroxyethyl)-N, N'-bis(4'-aminophenyl)-1,3-diaminopropan-2-ol, bis(2-hydroxy-5-aminophenyl)methane, 1,3-bis(2,5-diaminophenoxy)propan-2-ol, N,N'-bis(4'-aminophenyl)-1, 4-diazacycloheptane and 1,10-bis(2',5'-diaminophenyl)-1,4, 7,10-tetraoxadecane or one of their physiologically compatible salts.

In addition, it may be preferred according to the invention to use as developer component a p-aminophenol derivative or one of its physiologically compatible salts. Particular preference is given to p-aminophenol derivatives of the formula (E3)

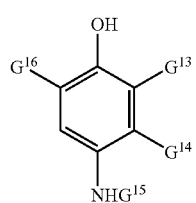

(E3)

where:

$G^{13}$ is a hydrogen atom, a halogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)-alkoxy($C_1$- to $C_4$)-alkyl radical, a $C_1$- to $C_4$-aminoalkyl radical, a hydroxy-($C_1$- to $C_4$)-alkylamino radical, a $C_1$- to $C_4$-hydroxyalkoxy radical, a $C_1$- to $C_4$-hydroxyalkyl-($C_1$- to $C_4$)-aminoalkyl radical or a (di-$C_1$- to $C_4$-alkylamino)-($C_1$- to $C_4$)-alkyl radical, and $G^{14}$ is a hydrogen or halogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)-alkoxy($C_1$- to $C_4$)-alkyl radical, a $C_1$- to $C_4$-aminoalkyl radical or a $C_1$- to $C_4$-cyanoalkyl radical, $G^{15}$ is hydrogen, a $C_1$- to $C_4$-alkyl radical, a $C_1$- to $C_4$-monohydroxyalkyl radical, a $C_2$- to $C_4$-polyhydroxyalkyl radical, a phenyl radical or a benzyl radical, and $G^{16}$ is hydrogen or a halogen atom.

According to the invention, the substituents used in formula (E3) are defined analogously to the above statements.

Preferred p-aminophenols of the formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(□-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol and their physiologically compatible salts.

Very particularly preferred compounds of the formula (E3) are p-aminophenol, 4-amino-3-methylphenol, 4-amino-2-aminomethylphenol, 4-amino-2-(α,β-dihydroxyethyl)phenol and 4-amino-2-(diethylaminomethyl)phenol.

In addition, the developer component can be chosen from o-aminophenol and its derivatives, such as, for example, 2-amino-4-methylphenol, 2-amino-5-methylphenol or 2-amino-4-chlorophenol.

In addition, the developer component can be chosen from heterocyclic developer components, such as, for example, the pyridine, pyrimidine, pyrazole, pyrazolepyrimidine derivatives and their physiologically compatible salts.

Preferred pyridine derivatives are, in particular, the compounds which are described in the patents GB 1 026 978 and GB 1,153,196, such as 2,5-diaminopyridine, 2-(4'-methoxyphenyl)amino-3-aminopyridine, 2,3-diamino-6-methoxypyridine, 2-(β-methoxyethyl)amino-3-amino-6-methoxypyridine and 3,4-diaminopyridine.

Preferred pyrimidine derivatives are, in particular, the compounds which are described in the German patent DE 2,359,399, the Japanese laid-open specification JP 02019576 A2 or in the laid-open specification WO 96/15765, such as 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Preferred pyrazole derivatives are, in particular, the compounds which are described in the patents DE 3,843,892, DE 4,133,957 and patent applications WO 94/08969, WO 94/08970, EP 740,931 and DE 195 43 988, such as 4,5-diamino-1-methylpyrazole, 4,5-diamino-1-(β-hydroxyethyl) pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-

(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole.

Preferred pyrazolopyrimidine derivatives are, in particular, the derivatives of the pyrazolo[1,5-a]pyrimidine of the following formula (E4) and its tautomeric forms provided there is a tautomeric equilibrium:

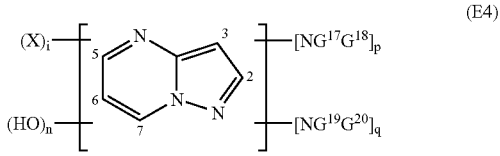

where:
G$^{17}$, G$^{18}$, G$^{19}$ and G$^{20}$, independently of one another, are a hydrogen atom, a C$_1$ to C$_4$-alkyl radical, an aryl radical, a C$_1$- to C$_4$-hydroxyalkyl radical, a C$_2$- to C$_4$-polyhydroxyalkyl radical, a (C$_1$- to C$_4$)-alkoxy(C$_1$- to C$_4$)-alkyl radical, a C$_1$- to C$_4$-alkylamino radical, which may be optionally protected by an acetyl, ureido or a sulfonyl radical, a (C$_1$- to C$_4$)-alkylamino-(C$_1$- to C$_4$)-alkyl radical, a di[(C$_1$- to C$_4$)-alkyl]-(C$_1$- to C$_4$)-aminoalkyl radical, where the dialkyl radicals optionally form a carbon cycle or a heterocycle having 5 or 6 chain members, a C$_1$- to C$_4$-hydroxyalkyl or a di(C$_1$- to C$_4$)-[hydroxyalkyl]-(C$_1$- to C$_4$)-aminoalkyl radical, the X radicals, independently of one another, are a hydrogen atom, a C$_1$- to C$_4$-alkyl radical, an aryl radical, a C$_1$- to C$_4$-hydroxyalkyl radical, a C$_2$- to C$_4$-polyhydroxyalkyl radical, a C$_1$- to C$_4$-aminoalkyl radical, a (C$_1$- to C$_4$)-alkylamino(C$_1$- to C$_4$)-alkyl radical, a di[(C$_1$- to C$_4$)alkyl]-(C$_1$- to C$_4$)-aminoalkyl radical, where the dialkyl radicals optionally form a carbon cycle or a heterocycle having 5 or 6 chain members, a C$_1$- to C$_4$-hydroxyalkyl radical or a di(C$_1$- to C$_4$-hydroxyalkyl)aminoalkyl radical, an amino radical, a C$_1$- to C$_4$-alkyl or di(C$_1$- to C$_4$-hydroxyalkyl)amino radical, a halogen atom, a carboxylic acid group or a sulfonic acid group, l has the value 0, 1, 2 or 3,
p has the value 0 or 1,
q has the value 0 or 1 and
n has the value 0 or 1, with the proviso that
the sum of p+q does not equal 0,
if p+q is 2, n has the value 0, and the groups NG$^{17}$G$^{18}$ and NG$^{19}$G$^{20}$ occupy the positions (2,3); (5,6); (6,7); (3,5) or (3,7);
if p+q is 1, n has the value 1, and the groups NG$^{17}$G$^{18}$ (or NG$^{19}$G$^{20}$) and the group OH occupy the positions (2,3); (5,6); (6,7); (3,5) or (3,7);

According to the invention, the substituents used in formula (E4) are defined analogously to the above statements.

If the pyrazolo[1,5-a]pyrimidine of the above formula (E4) comprises a hydroxy group in one of the positions 2, 5 or 7 of the ring system, there is a tautomeric equilibrium, which is represented, for example, in the following scheme:

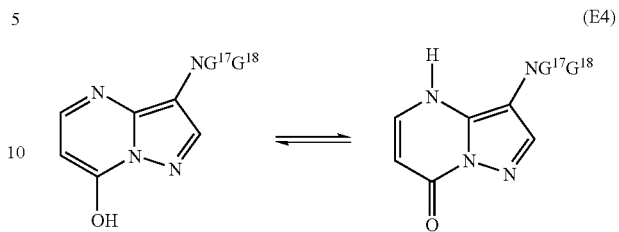

Among the pyrazolo[1,5-a]pyrimidines of the above formula (E4), mention may be made in particular, of:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)(2-hydroxyethyl)amino]ethanol;
2-[(7-aminopyrazolo[1,5-a]pyrimidin-3-yl)(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
3-amino-7-dimethylamino-2,5-dimethylpyrazolo[1,5-a]pyrimidine;

and their physiologically compatible salts and their tautomeric forms if a tautomeric equilibrium is present.

The pyrazolo[1,5-a]pyrimidines of the above formula (E4) can be prepared as described in the literature by cyclization starting from an aminopyrazole or from hydrazine.

The precursors of nature-analogous dyes used are preferably those indoles and indolines which have at least one hydroxy or amino group, preferably as substituent on the six-membered ring. These groups can carry further substituents, e.g., in the form of an etherification or esterification of the hydroxy group or an alkylation of the amino group. These indoles and indolines can be used as developer component in oxidation hair colors.

Of particularly good suitability as precursors of nature-analogous hair dyes are derivatives of 5,6-dihydroxyindoline of the formula (Ia),

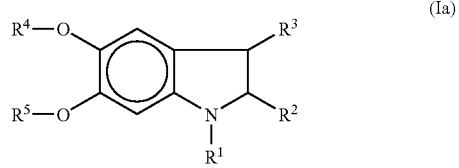

in which, independently of one another,
R$^1$ is hydrogen, a C$_1$-C$_4$-alkyl group or a C$_1$-C$_4$-hydroxyalkyl group,
R$^2$ is hydrogen or a —COOH group, where the —COOH group may also be present as salt with a physiologically compatible cation,
R$^3$ is hydrogen or a C$_1$-C$_4$-alkyl group, R⁴ is hydrogen, a $C_1$-$C_4$-alkyl group or a group —CO—R⁶, in which R⁶ is a $C_1$-$C_4$-alkyl group, and R⁵ is one of the groups specified under R⁴, and physiologically compatible salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid and 6-hydroxyindoline, 6-aminoindoline and 4-aminoindoline.

Within this group, emphasis is placed particularly on N-methyl-5,6-dihydroxyindoline, N-ethyl-5,6-dihydroxyindoline, N-propyl-5,6-dihydroxyindoline, N-butyl-5,6-dihydroxyindoline and, in particular, 5,6-dihydroxyindoline.

Of exceptional suitability as precursors of nature-analogous hair dyes are also derivatives of 5,6-hydroxyindole of the formula (Ib),

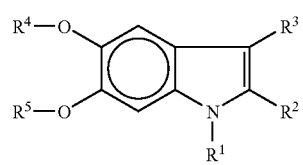

in which, independently of one another,

R¹ is hydrogen, a $C_1$-$C_4$-alkyl group or a $C_1$-$C_4$-hydroxyalkyl group,

R² is hydrogen or a —COOH group, where the —COOH group may also be present as salt with a physiologically compatible cation, R³ is hydrogen or a $C_1$-$C_4$-alkyl group, R⁴ is hydrogen, a $C_1$-$C_4$-alkyl group or a group —CO—R⁶, in which R⁶ is a $C_1$-$C_4$-alkyl group, and R⁵ is one of the groups specified under R⁴, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, emphasis is given to N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole.

In the dyeing compositions used within the scope of the method according to the invention, the indoline and indole derivatives can be used either as free bases or else in the form of their physiologically compatible salts with inorganic or organic acids, e.g., the hydrochlorides, the sulfates and hydrobromides. The indole or indoline derivatives are present in these usually in amounts of from 0.05-10% by weight, preferably 0.2-5% by weight.

In a further embodiment, it may be preferred according to the invention to use the indoline or indole derivative in hair dyeing compositions in combination with at least one amino acid or an oligopeptide. The amino acid is advantageously an α-amino acid; very particularly preferred α-amino acids are arginine, ornithine, lysine, serine and histidine, in particular, arginine.

In a further preferred embodiment, the dyeing compositions of the process according to the invention comprise at least one coupler component.

The coupler components used are generally m-phenylenediamine derivatives, naphthols, resorcinol and resorcinol derivatives, pyrazolones and m-aminophenol derivatives, and heterocyclic compounds.

Coupler components preferred according to the invention are m-aminophenol and derivatives thereof, such as, for example, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-3-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol and 2,4-dichloro-3-aminophenol, o-aminophenol and derivatives thereof, m-diaminobenzene and derivatives thereof, such as, for example, 2,4-diaminophenoxyethanol, 1,3-bis(2',4'-diaminophenoxy)propane, 1-methoxy-2-amino-4-(2'-hydroxyethylamino)benzene, 1,3-bis(2',4'-diaminophenyl)propane, 2,6-bis(2'-hydroxyethylamino)-1-methylbenzene and 1-amino-3-bis(2'-hydroxyethyl)aminobenzene, o-diaminobenzene and derivatives thereof, such as, for example, 3,4-diaminobenzoic acid and 2,3-diamino-1-methylbenzene, di- or trihydroxybenzene derivatives, such as, for example, resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene, pyridine derivatives, such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, naphthalene derivatives, such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene, morpholine derivatives, such as, for example, 6-hydroxybenzomorpholine and 6-aminobenzomorpholine, quinoxaline derivatives, such as, for example, 6-methyl-1,2,3,4-tetrahydroquinoxaline, pyrazole derivatives, such as, for example, 1-phenyl-3-methylpyrazol-5-one, indole derivatives, such as, for example, 4-hydroxyindole, 6-hydroxyindole and 7-hydroxyindole, pyrimidine derivatives, such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine, or methylenedioxybenzene derivatives such as, for example, 1-hydroxy-3,4-methylenedioxybenzene, 1-amino-3,4-methylenedioxybenzene and 1-(2'-hydroxyethyl)amino-3,4-methylenedioxybenzene.

Coupler components particularly preferred according to the invention are 1-naphthol, 1,5-dihydroxynaphthalene, 2,7-dihydroxynaphthalene, 1,7-dihydroxynaphthalene, 5-amino-2-methylphenol, m-aminophenol, resorcinol, m-phenylenediamine, 1-phenyl-3-methylpyrazol-5-one, 2,4-dichloro-3-aminophenol, 1,3-bis(2,4-diaminophenoxy)propane, 2-chlororesorcinol, 4-chlororesorcinol, 2-chloro-6-methyl-3-aminophenol, 3-amino-2-methylamino-6-methoxypyridine, 2-amino-3-hydroxypyridine, 2,6-dihydroxy-3,4-dimethylpyridine, 2-methylresorcinol, 5-methylresorcinol, 2-methyl-4-chloro-5-aminophenol and the physiologically compatible salts of the above-mentioned compounds.

It is particularly preferred to formulate the dyeing compositions in such a way that, after carrying out the method according to the invention, one of the 10 color pairs for the starting coloration and the oxidatively nuanced hair as in TABLE 1 arises:

TABLE 1

| No. | Color of the starting coloration (after step A) | Color following oxidative lightening (after step C) |
|---|---|---|
| 1 | mid-blonde | blonde |
| 2 | dark blonde | pale blonde |
| 3 | red | red-orange |
| 4 | red | pale red |
| 5 | copper-red | pale copper-blonde |
| 6 | violet | dark pink |
| 7 | gold-brown | gold-blonde |
| 8 | mid-brown | brown-blonde |
| 9 | dark brown | pale brown |
| 10 | black-brown | brown |

Surprisingly, it has been found that the following combinations of oxidation dye precursors are particularly well suited for preparing color pairs with blonde starting coloration (color pair 1 and 2 according to TABLE 1):
  at least one p-phenylenediamine derivative according to formula (E1)
  at least one p-aminophenol derivative according to formula (E3)
  at least one pyridine derivative as coupler
  at least one compound chosen from m-aminophenol or its derivatives as coupler.

Surprisingly, it has been found that the following combinations of oxidation dye precursors are particularly well suited for preparing color pairs with red starting coloration (color pairs 3, 4 and 5 according to TABLE 1):
  at least one heterocyclic developer chosen from pyrazole derivatives and pyrimidine derivatives
  at least two compounds chosen from m-aminophenol and its derivatives as coupler.

Surprisingly, it has been found that the following combinations of oxidation dye precursors are particularly well suited for preparing color pairs with violet starting color (color pair 6 according to Table 1):
  at least one pyrazole derivative as developer
  at least one pyridine derivative as coupler
  at least one compound chosen from m-aminophenol and its derivatives as coupler.

Surprisingly, it has been found that the following combinations of oxidation dye precursors are particularly well suited for preparing color pairs with brown starting coloration (color pairs 7, 8, 9 and 10 according to TABLE 1):
  at least one p-phenylenediamine derivative according to formula (E1)
  at least one pyridine derivative as coupler
  at least one compound chosen from m-aminophenol or its derivatives as coupler.

For forming the color pairs, the above-mentioned preferred oxidation dye precursors are used in the above-mentioned combinations as preferred developers and couplers.

The dyeing compositions of the method according to the invention comprise both the developer components and also the coupler components preferably in an amount of from 0.005 to 10% by weight, preferably from 0.1 to 5% by weight, in each case based on the overall oxidation dyeing composition.

Here, developer components and coupler components are generally used in approximately molar amounts relative to one another. Although the molar use has also proven to be expedient, a certain excess of individual oxidation dye precursors is not disadvantageous, meaning that developer components and coupler components may be present in a molar ratio of from 1:0.5 to 1:3, in particular, 1:1 to 1:2.

For the nuancing, the dyeing compositions of the method according to the invention can comprise one or more direct dyes. Direct dyes are usually nitrophenylenediamines, nitroaminophenols, azo dyes, anthraquinones or indophenols. Preferred direct dyes are the compounds known under the international names or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1 and Acid Black 52, and 1,4-diamino-2-nitrobenzene, 2-amino-4-nitrophenol, 1,4-bis(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-1-hydroxy-4-nitrobenzene.

In addition, the dyeing compositions can comprise a cationic direct dye. Particular preference is given here to
  (a) cationic triphenylmethane dyes, such as, for example, Basic Blue 7, Basic Blue 26, Basic Violet 2 and Basic Violet 14, (b) aromatic systems which are substituted by a quaternary nitrogen group, such as, for example, Basic Yellow 57, Basic Red 76, Basic Blue 99, Basic Brown 16 and Basic Brown 17, and (c) direct dyes which contain a heterocycle which has at least one quaternary nitrogen atom, as are specified, for example, in EP-A2-998,908.

Preferred cationic direct dyes of group (c) are, in particular, the following compounds:

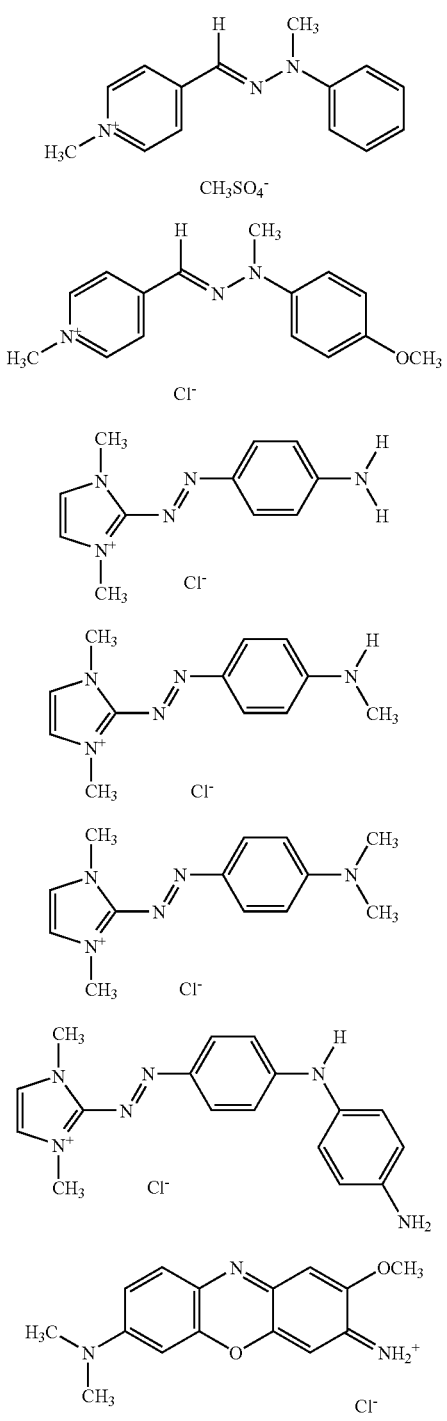

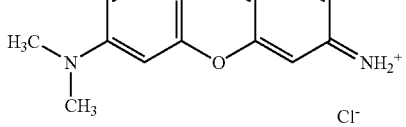

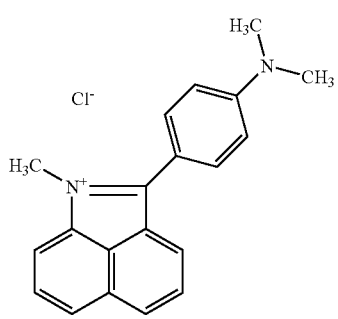

The compounds of the formulas (DZ1), (DZ3) and (DZ5), which are also known under the names Basic Yellow 87, Basic Orange 31 and Basic Red 51, are very particularly preferred cationic direct dyes of group (c).

The cationic direct dyes which are sold under the trade name Arianor® are likewise very particularly preferred cationic direct dyes according to the invention.

The dyeing compositions can comprise the direct dyes in an amount of from 0.1 to 5% by weight, based on the overall dyeing composition.

In addition, the dyeing compositions of the method according to the invention can also comprise naturally occurring dyes as are present, for example, in Henna red, Henna neutral, Henna black, camomile blossom, sandalwood, black tea, buckthorn bark, sage, logwood, madder root, catechu, sedre and alkanna root.

However, it is preferred according to the invention that the dyeing compositions used in the method according to the invention comprise no direct dyes.

It is not necessary for the oxidation dye precursors or the direct dyes to in each case constitute uniform compounds. Rather, as a result of the preparation methods for the individual dyes, it is possible for the hair dyeing compositions according to the invention to also comprise further components in minor amounts provided these do not adversely affect the coloring result or have to be excluded for other reasons, e.g,. toxicological reasons.

With regard to the dyes which can be used in the coloring composition of the method according to the invention, reference is also expressly made to the monograph Ch. Zviak, The Science of Hair Care, chapter 7 (pages 248-250; direct dyes), and chapter 8, pages 264-267; oxidation dye precursors), published as volume 7 of the "Dermatology" series (ed.: Ch., Culnan and H. Maibach), Verlag Marcel Dekker Inc., New York, Basle, 1986, and the "European inventory of cosmetic raw materials", published by the European Community, obtainable in diskette form from the Bundesverband Deutscher Industrie- und Handelsuntemehmen für Arzneimittel, Reformwaren und Körperpflegemittel e.V., Mannheim.

The dyeing composition of the method according to the invention can comprise, as color-imparting component, at least one combination, preferably a three-fold combination, chosen from the components A compounds which comprise a reactive carbonyl group with component B compounds chosen from (a) CH-acidic compounds, (b) compounds with primary or secondary amino group or hydroxy group, chosen from primary or secondary aromatic amines, nitrogen-containing heterocyclic compounds and aromatic hydroxy compounds, (c) amino acids, and (d) oligopeptides constructed from 2 to 9 amino acids, where at least one representative of this combination has to be a compound with a reactive carbonyl group according to component A.

Compounds according to the invention with a reactive carbonyl group (also termed below reactive carbonyl compounds or component A) have at least one carbonyl group as reactive group which reacts with the compounds of component B to form a chemical bond linking the two components. In addition, the invention also covers those compounds as component A in which the reactive carbonyl group is derivatized or masked in such a way that the reactivity of the carbon atoms of the derivatized or masked carbonyl group toward the component B is always present. These derivatives are preferably condensation compounds of reactive carbonyl compounds with a) amines and derivatives thereof with the formation of imines or oximes as condensation compound b) alcohols with the formation of acetals or ketals as condensation compound c) water with the formation of hydrates as condensation compound of aldehydes.

Component A is preferably chosen from the group which is formed from acetophenone, propiophenone, 2-hydroxyacetophenone, 3-hydroxyacetophenone, 4-hydroxyacetophenone, 2-hydroxypropiophenone, 3-hydroxypropiophenone, 4-hydroxypropiophenone, 2-hydroxybutyrophenone, 3-hydroxybutyrophenone, 4-hydroxybutyrophenone, 2,4-dihydroxyacetophenone, 2,5-dihydroxyacetophenone, 2,6-dihydroxyacetophenone, 2,3,4-trihydroxyacetophenone, 3,4,5-trihydroxyacetophenone, 2,4,6-trihydroxyacetophenone, 2,4,6-trimethoxyacetophenone, 3,4,5-trimethoxyacetophenone, 3,4,5-trimethoxyacetophenone diethyl ketal, 4-hydroxy-3-methoxyacetophenone, 3,5-dimethoxy-4-hydroxyacetophenone, 4-aminoacetophenone, 4-dimethylaminoacetophenone, 4-morpholinoacetophenone, 4-piperidinoacetophenone, 4-imidazolinoacetophenone, 2-hydroxy-5-bromoacetophenone, 4-hydroxy-3-nitroacetophenone, acetophenone-2-carboxylic acid, acetophenone-4-carboxylic acid, benzophenone, 4-hydroxybenzophenone, 2-aminobenzophenone, 4,4'-dihydroxybenzophenone, 2,4-dihydroxybenzophenone, 2,4,4'-trihydroxybenzophenone, 2,3,4-trihydroxybenzophenone, 2-hydroxy-1-acetonaphthone, 1-hydroxy-2-acetonaphthone, chromone, chromone-2-carboxylic acid, flavone, 3-hydroxyflavone, 3,5,7-trihydroxyflavone, 4',5,7-trihydroxyflavone, 5,6,7-trihydroxyflavone, quercetin, 1-indanone, 9-fluorenone, 3-hydroxyfluorenone, anthrone, 1,8-dihydroxyanthrone, vanillin, coniferylaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-3-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 4-hydroxy-3,5-dimethoxybenzaldehyde, 4-hydroxy-3,5-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,5-dihydroxybenzaldehyde, 2,6-dihydroxybenzaldehyde, 3,4-dihydroxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-hydroxy-2-methoxybenzaldehyde, 4-dimethylaminobenzaldehyde, 4-diethylaminobenzaldehyde, 4-dimethylamino-2-hydroxybenzaldehyde, 4-diethylamino-2-hydroxybenzaldehyde, 4-pyrrolidinobenzaldehyde, 4-morpholinobenzaldehyde, 2-morpholinobenzaldehyde, 4-piperidinobenzaldehyde, 2-methoxy-1-naphthaldehyde, 4-methoxy-1-naphthaldehyde, 2-hydroxy-1-naphthaldehyde, 2,4-dihydroxy-1-naphthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-hydroxy-1-naphthaldehyde, 4-dimethylamino-1-naphthaldehyde, 2-methoxycinnamaldehyde, 4-methoxycinnamaldehyde, 4-hydroxy-3-methoxycinnamaldehyde, 3,5-dimethoxy-4-hydroxycinnamaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 4-diphenylaminobenzaldehyde, 4-dimethylamino-2-methoxybenzaldehyde, 4-(1-imidazolyl)benzaldehyde, piperonal, 2,3,6,7-tetrahydro-1H,5H-benzo[ij]quinolizine-9-carboxaldehyde, 2,3,6,7-tetrahydro-8-hydroxy-1H,5H-benzo[ij]quinolizine-9-carboxaldehyde, N-ethylcarbazole-3-aldehyde, 2-formylmethylene-1,3,3-trimethylindoline (Fischers aldehyde or tribase aldehyde), 2-indolealdehyde, 3-indolealdehyde, 1-methylindole-3-aldehyde, 2-methylindole-3-aldehyde, 1-acetylindole-3-aldehyde, 3-acetylindole, 1-methyl-3-acetylindole, 2-(1',3',3'-trimethyl-2-indolinylidene)acetaldehyde, 1-methylpyrrole-2-aldehyde, 1-methyl-2-acetylpyrrole, 4-pyridinealdehyde, 2-pyridinealdehyde, 3-pyridinealdehyde, 4-acetylpyridine, 2-acetylpyridine, 3-acetylpyridine, pyridoxal, quinoline-3-aldehyde, quinoline-4-aldehyde, antipyrine-4-aldehyde, furfural, 5-nitrofurfural, 2-thenoyltrifluoroacetone, chromone-3-aldehyde, 3-(5'-nitro-2'-furyl)acrolein, 3-(2'-furyl)acrolein and imidazole-2-aldehyde, 1,3-diacetylbenzene, 1,4-diacetylbenzene, 1,3,5-triacetylbenzene, 2-benzoylacetophenone, 2-(4'-methoxybenzoyl)acetophenone, 2-(2'-furoyl)acetophenone, 2-(2'-pyridoyl)acetophenone and 2-(3'-pyridoyl)acetophenone, benzylideneacetone, 4-hydroxybenzylideneacetone, 2-hydroxybenzylideneacetone, 4-methoxybenzylideneacetone, 4-hydroxy-3-methoxybenzylideneacetone, 4-dimethylaminobenzylideneacetone, 3,4-methylenedioxybenzylideneacetone, 4-pyrrolidinobenzylideneacetone, 4-piperidinobenzylideneacetone, 4-morpholinobenzylideneacetone, 4-diethylaminobenzylideneacetone, 3-benzylidene-2,4-pentanedione, 3-(4'-hydroxybenzylidene)-2,4-pentanedione, 3-(4'-dimethylaminobenzylidene)-2,4-pentanedione, 2-benzylidenecyclohexanone, 2-(4'-hydroxybenzylidene)cyclohexanone, 2-(4'-dimethylaminobenzylidene)cyclohexanone, 2-benzylidene-1,3-cyclohexanedione, 2-(4'-hydroxybenzylidene)-1,3-cyclohexanedione, 3-(4'-dimethylaminobenzylidene)-1,3-cyclohexanedione, 2-benzylidene-5,5-dimethyl-1,3-cyclohexanedione, 2-(4'-hydroxybenzylidene)-5,5-dimethyl-1,3-cyclohexanedione, 2-(4'-hydroxy-3-methoxybenzylidene)-5,5-dimethyl-1,3-cyclohexanedione, 2-(4'-dimethylaminobenzylidene)-5,5-dimethyl-1,3-cyclohexanedione, 2-benzylidenecyclopentanone, 2'-(4-hydroxybenzylidene)cyclopentanone, 2-(4'-dimethylaminobenzylidene)cyclopentanone, 5-(4-dimethylaminophenyl)penta-2,4-dienal, 5-(4-diethylaminophenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal, 5-(4-morpholinophenyl)penta-2,4-dienal, 5-(4-pyrrolidinophenyl)penta-2,4-dienal, 6-(4-dimethylaminophenyl)hexa-3,5-dien-2-one, 6-(4-diethylaminophenyl)hexa-3,5-dien-2-one, 6-(4-methoxyphenyl)hexa-3,5-dien-2-one, 6-(3,4-dimethoxyphenyl)hexa-3,5-dien-2-one, 6-(2,4-dimethoxyphenyl)hexa-3,5-dien-2-one, 6-(4-piperidinophenyl)hexa-3,5-dien-2-one, 6-(4-morpholinophenyl)hexa-3,5-dien-2-one, 6-(4-pyrrolidinophenyl)hexa-3,5-dien-2-one, 5-(4-dimethylamino-1-naphthyl)penta-3,5-dienal, 2-nitrobenzaldehyde, 3-nitrobenzaldehyde, 4-nitrobenzaldehyde, 4-methyl-3-nitrobenzaldehyde, 3-hydroxy-4-nitrobenzaldehyde, 4-hydroxy-3-nitrobenzaldehyde, 5-hydroxy-2-nitrobenzaldehyde, 2-hydroxy-5-nitrobenzaldehyde, 2-hydroxy-3-nitrobenzaldehyde, 2-fluoro-3-nitrobenzaldehyde, 3-methoxy-2-nitrobenzaldehyde, 4-chloro-3-nitrobenzaldehyde, 2-chloro-6-nitrobenzaldehyde, 5-chloro-2-nitrobenzaldehyde, 4-chloro-2-nitrobenzaldehyde, 2,4-dinitrobenzaldehyde, 2,6-dinitrobenzaldehyde, 2-hydroxy-3-methoxy-5-nitrobenzaldehyde, 4,5-dimethoxy-2-nitrobenzaldehyde, 6-nitropiperonal, 2-nitropiperonal, 5-nitrovanillin, 2,5-dinitrosalicylaldehyde, 5-bromo-3-nitrosalicylaldehyde, 3-nitro-4-formylbenzenesulfonic acid, 4-nitro-1-naphthaldehyde, 2-nitrocinnamaldehyde, 3-nitrocinnamaldehyde, 4-nitrocinnamaldehyde, 9-methyl-3-carbazolealdehyde, 9-ethyl-3-carbazolealdehyde, 3-acetylcarbazole, 3,6-diacetyl-9-ethylcarbazole, 3-acetyl-9-methylcarbazole, 1,4-dimethyl-3-carbazolealdehyde, 1,4,9-trimethyl-3-carbazolealdehyde, 4-formyl-1-methylpyridinium-, 2-formyl-1-methylpyridinium-, 4-formyl-1-ethylpyridinium-, 2-formyl-1-ethylpyridinium-, 4-formyl-1-benzylpyridinium-, 2-formyl-1-benzylpyridinium-, 4-formyl-1,2-dimethylpyridinium-, 4-formyl-1,3-dimethylpyridinium-, 4-formyl-1-methylquinolinium-, 2-formyl-1-methylquinolinium-, 4-acetyl-1-methylpyridinium-, 2-acetyl-1-methylpyridinium-, 4-acetyl-1-methylquinolinium-, 5-formyl-1-methylquinolinium-, 6-formyl-1-methylquinolinium-, 7-formyl-1-methylquinolinium-, 8-formyl-1-methylquinolinium, 5-formyl-1-ethylquinolinium-, 6-formyl-1-ethylquinolinium-, 7-formyl-1-ethylquinolinium-, 8-formyl-1-ethylquinolinium, 5-formyl-1-benzylquinolinium-, 6-formyl-1-benzylquinolinium-, 7-formyl-1-benzylquinolinium-, 8-formyl-1-benzylquinolinium, 5-formyl-1-allylquinolinium-, 6-formyl-1-allylquinolinium-, 7-formyl-1-allylquinolinium- and 8-formyl-1-allylquinolinium-, 5-acetyl-1-methylquinolinium-, 6-acetyl-1-methylquinolinium-, 7-acetyl-1-methylquinolinium-, 8-acetyl-1-methylquinolinium-, 5-acetyl-1-ethylquinolinium-, 6-acetyl-1-ethylquinolinium-, 7-acetyl-1-ethylquinolinium-, 8-acetyl-1-ethylquinolinium-, 5-acetyl-1-benzylquinolinium-, 6-acetyl-1-benzylquinolinium-, 7-acetyl-1-benzylquinolinium-, 8-acetyl-1-benzylquinolinium-, 5-acetyl-1-allylquinolinium-, 6-acetyl-1-allylquinolinium-, 7-acetyl-1-allylquinolinium- and 8-acetyl-1-allylquinolinium-, 9-formyl-10-methylacridinium-, 4-(2'-formylvinyl)-1-methylpyridinium-, 1,3-dimethyl-2-(4'-formylphenyl)benzimidazolium-, 1,3-dimethyl-2-(4'-formylphenyl)imidazolium-, 2-(4'-formylphenyl)-3-methylbenzothiazolium-, 2-(4'-acetylphenyl)-3-methylbenzothiazolium-, 2-(4'-formylphenyl)-3-methylbenzoxazolium-, 2-(5'-formyl-2'-furyl)-3-methylbenzothiazolium-, 2-(5'-formyl-2'-furyl)-3-methylbenzothiazolium-, 2-(5'-formyl-2'-thienyl)-3-methylbenzothiazolium-, 2-(3'-formylphenyl)-3-methylbenzothiazolium-, 2-(4'-formyl-1-naphthyl)-3-methylbenzothiazolium-, 5-chloro-2-(4'-formylphenyl)-3-methylbenzothiazolium-, 2-(4'-formylphenyl)-3,5-dimethylbenzothiazolium benzenesulfonate, p-toluenesulfonate, methanesulfonate, perchlorate, sulfate, chloride, bromide, iodide, tetrachlorozincate, methylsulfate, trifluoromethanesulfonate, tetrafluoroborate, isatin, 1-methylisatin, 1-allylisatin, 1-hydroxymethylisatin, 5-chloroisatin, 5-methoxyisatin, 5-nitroisatin, 6-nitroisatin, 5-sulfoisatin, 5-carboxyisatin, quinisatin, 1-methylquinisatin, and any mixtures of the above compounds.

CH-acidic compounds are generally regarded as being those compounds which carry a hydrogen atom bonded to an aliphatic carbon atom with electron-attracting substituents resulting in activation of the corresponding carbon-hydrogen bond. CH-acidic compounds according to the invention also include enamines, which are produced by alkaline treatment of quaternized N-heterocycles with a CH-acidic alkyl group positioned in conjugation to the quaternary nitrogen.

The CH-acidic compounds of component B are preferably chosen from the group consisting of 1,2,3,3-tetramethyl-3H-indolium iodide, 1,2,3,3-tetramethyl-3H-indolium p-toluenesulfonate, 1,2,3,3-tetramethyl-3H-indolium methanesulfonate, 1,3,3-trimethyl-2-methyleneindoline (Fischers base), 2,3-dimethylbenzothiazolium iodide, 2,3-dimethylbenzothiazolium p-toluenesulfonate, 2,3-dimethylnaphtho[1,2-d]thiazolium p-toluenesulfonate, 3-ethyl-2-methylnaphtho[1,2-d]thiazolium p-toluenesulfonate, rhodanine, rhodanine-3-acetic acid, 1,4-dimethylquinolinium iodide, 1,2-dimethylquinolinium iodide, barbituric acid, thiobarbituric acid, 1,3-dimethylthiobarbituric acid, 1,3-diethylthiobarbituric acid, 1,3-diethylbarbituric acid, oxindole, 3-indoxylacetate, 2-coumaranone, 5-hydroxy-2-coumaranone, 6-hydroxy-2-coumaranone, 3-methyl-1-phenylpyrazolin-5-one, indane-1,2-dione, indane-1,3-dione, indan-1-one, benzoylacetonitrile, 3-dicyanomethyleneindan-1-one, 2-amino-4-imino-1,3-thiazoline hydrochloride, 5,5-dimethylcyclohexane-1,3-dione, 2H-1,4-benzoxazin-4H-3-one, 3-ethyl-2-methylbenzoxazolium iodide, 3-ethyl-2-methylbenzothiazolium iodide, 1-ethyl-4-methylquinolinium iodide, 1-ethyl-2-methylquinolinium iodide, 1,2,3-trimethylquinoxalinium iodide, 3-ethyl-2-methylbenzoxazolium p-toluenesulfonate, 3-ethyl-2-methylbenzothiazolium p-toluenesulfonate, 1-ethyl-4-methylquinolinium p-toluenesulfonate, 1-ethyl-2-methylquinolinium p-toluenesulfonate, and 1,2,3-trimethylquinoxalinium p-toluenesulfonate.

Preferred primary or secondary aromatic amines of component B are chosen from N,N-dimethyl-p-phenylenediamine, N,N-diethyl-p-phenylenediamine, N-(2-hydroxyethyl)-N-ethyl-p-phenylenediamine, N,N-bis(2-hydroxyethyl)-p-phenylenediamine, N-(2-methoxyethyl)-p- phenylenediamine, 2,3-dichloro-p-phenylenediamine, 2,4-dichloro-p-phenylenediamine, 2,5-dichloro-p-phenylenediamine, 2-chloro-p-phenylenediamine, 2,5-dihydroxy-4-morpholinoaniline, 2-aminophenol, 3-aminophenol, 4-aminophenol, 2-aminomethyl-4-aminophenol, 2-hydroxymethyl-4-aminophenol, o-phenylenediamine, m-phenylenediamine, p-phenylenediamine, 2,5-diaminotoluene, 2,5-diaminophenol, 2,5-diaminoanisole, 2,5-diaminophenethol, 4-amino-3-methylphenol, 2-(2,5-diaminophenyl)ethanol, 2,4-diaminophenoxyethanol, 2-(2,5-diaminophenoxy)ethanol, 3-amino-4-(2-hydroxyethyloxy)phenol, 3,4-methylenedioxyphenol, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 3-amino-2-chloro-6-methylphenol, 2-methyl-5-amino-4-chlorophenol, 5-(2-hydroxyethylamino)-4-methoxy-2-methylphenol, 4-amino-2-hydroxymethylphenol, 2-(diethylaminomethyl)-4-aminophenol, 4-amino-1-hydroxy-2-(2-hydroxyethylaminomethyl)benzene, 1-hydroxy-2-amino-5-methylbenzene, 1-hydroxy-2-amino-6-methylbenzene, 2-amino-5-acetamidophenol, 1,3-dimethyl-2,5-diaminobenzene, 5-(3-hydroxypropylamino)-2-methylphenol, 5-amino-4-methoxy-2-methylphenol, N,N-dimethyl-3-aminophenol, N-cyclopentyl-3-aminophenol, 5-amino-4-fluoro-2-methylphenol, 2,4-diamino-5-fluorotoluene, 2,4-diamino-5-(2-hydroxyethoxy)toluene, 2,4-diamino-5-methylphenetol, 3,5-diamino-2-methoxy-1-methylbenzene, 2-amino-4-(2-hydroxyethylamino)anisole, 2,6-bis(2-hydroxyethylamine)-1-methylbenzene, 1,3-diamino-2,4-dimethoxybenzene, 3,5-diamino-2-methoxytoluene, 2-aminobenzoic acid, 3-aminobenzoic acid, 4-aminobenzoic acid, 2-aminophenylacetic acid, 3-aminophenylacetic acid, 4-aminophenylacetic acid, 2,3-diaminobenzoic acid, 2,4-diaminobenzoic acid, 2,5-diaminobenzoic acid, 3,4-diaminobenzoic acid, 3,5-diaminobenzoic acid, 4-aminosalicylic acid, 5-aminosalicylic acid, 3-amino-4-hydroxybenzoic acid, 4-amino-3-hydroxybenzoic acid, 2-aminobenzenesulfonic acid, 3-aminobenzenesulfonic acid, 4-aminobenzenesulfonic acid, 3-amino-4-hydroxybenzenesulfonic acid, 4-amino-3-hydroxynaphthalene-1-sulfonic acid, 6-amino-7-hydroxynaphthalene-2-sulfonic acid, 7-amino-4-hydroxynaphthalene-2-sulfonic acid, 4-amino-5-hydroxynaphthalene-2,7-disulfonic acid, 3-amino-2-naphthoic acid, 3-aminophthalic acid, 5-aminoisophthalic acid, 1,3,5-triaminobenzene, 1,2,4-triaminobenzene, 1,2,4,5-tetraminobenzene, 2,4,5-triaminophenol, pentaminobenzene, hexaminobenzene, 2,4,6-triaminoresorcinol, 4,5-diaminopyrocatechin, 4,6-diaminopyrogallol, 1-(2-hydroxy-5-aminobenzyl)-2-imidazolidinone, 4-amino-2-((4-[(5-amino-2-hydroxyphenyl)methyl]piperazinyl)methyl)phenol, 3,5-diamino-4-hydroxypyrocatechin, 1,4-bis(4-aminophenyl)-1,4-diazacycloheptane, aromatic nitriles, such as 2-amino-4-hydroxybenzonitrile, 4-amino-2-hydroxybenzonitrile, 4-aminobenzonitrile, 2,4-diaminobenzonitrile, nitro group-containing amino compounds, such as 3-amino-6-methylamino-2-nitropyridine, picramic acid, [8-[(4-amino-2-nitrophenyl)azo]-7-hydroxynaphth-2-yl]trimethylammonium chloride, [8-((4-amino-3-nitrophenyl)azo)-7-hydroxynaphth-2-yl]trimethylammonium chloride (Basic Brown 17), 1-hydroxy-2-amino-4,6-dinitrobenzene, 1-amino-2-nitro-4-[bis(2-hydroxyethyl)amino]benzene, 1-amino-2-[(2-hydroxyethyl)amino]-5-nitrobenzene (HC Yellow No. 5), 1-amino-2-nitro-4-[(2-hydroxyethyl)amino]benzene (HC Red No. 7), 2-chloro-5-nitro-N-2-hydroxyethyl-1,4-phenylenediamine, 1-[(2-hydroxyethyl)amino]-2-nitro-4-aminobenzene (HC Red No. 3), 4-amino-3-nitrophenol, 4-amino-2-nitrophenol, 6-nitro-o-toluidine, 1-amino-3-methyl-4-[(2-hydroxyethyl)amino]-6-nitrobenzene (HC Violet No. 1), 1-amino-2-nitro-4-[(2,3-dihydroxypropyl)amino]-5-chlorobenzene (HC Red No. 10), 2-(4-amino-2-nitroanilino) benzoic acid, 6-nitro-2,5-diaminopyridine, 2-amino-6-chloro-4-nitrophenol, 1-amino-2-(3-nitrophenylazo)-7-phenylazo-8-naphthol-3,6-disulfonic acid disodium salt (Acid Blue No. 29), 1-amino-2-(2-hydroxy-4-nitrophenylazo)-8-naphthol-3,6-disulfonic acid disodium salt (Palatine chrome green), 1-amino-2-(3-chloro-2-hydroxy-5-nitrophenylazo)-8-naphthol-3,6-disulfonic acid disodium salt (Gallion), 4-amino-4'-nitrostilbene-2,2'-disulfonic acid disodium salt, 2,4-diamino-3',5'-dinitro-2'-hydroxy-5-methylazobenzene (Mordant brown 4), 4'-amino-4-nitrodiphenylamine-2-sulfonic acid, 4'-amino-3'-nitrobenzophenone-2-carboxylic acid, 1-amino-4-nitro-2-(2-nitrobenzylideneamino)benzene, 2-[2-(diethylamino)ethylamino]-5-nitroaniline, 3-amino-4-hydroxy-5-nitrobenzenesulfonic acid, 3-amino-3'-nitrobiphenyl, 3-amino-4-nitroacenaphthene, 2-amino-1-nitronaphthalene, 5-amino-6-nitrobenzo-1,3-dioxole, anilines, in particular, nitro group-containing anilines, such as 4-nitroaniline, 2-nitroaniline, 1,4-diamino-2-nitrobenzene, 1,2-diamino-4-nitrobenzene, 1-amino-2-methyl-6-nitrobenzene, 4-nitro-1,3-phenylenediamine, 2-nitro-4-amino-1-(2-hydroxyethylamino)benzene, 2-nitro-1-amino-4-[bis(2-hydroxyethyl)amino]benzene, 4-amino-2-nitrodiphenylamine-2'-carboxylic acid, 1-amino-5-chloro-4-(2-hydroxyethylamino)-2-nitrobenzene, aromatic anilines and phenols with a further aromatic radical, as shown in the formula II

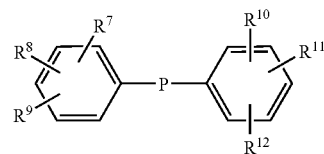

(II)

in which
R$^7$ is a hydroxy or an amino group which may be substituted by $C_{1-4}$-alkyl, $C_{1-4}$-hydroxyalkyl, $C_{1-4}$-alkoxy or $C_{1-4}$-alkoxy-$C_{1-4}$-alkyl groups,
R$^8$, R$^9$, R$^{10}$, R$^{11}$ and R$^{12}$, independently of one another, are a hydrogen atom, a hydroxy or an amino group which may be substituted by $C_1$-$C_4$-alkyl, $C_1$-$C_4$-hydroxyalkyl, $C_1$-$C_4$-alkoxy, $C_1$-$C_4$-aminoalkyl or $C_1$-$C_4$-alkoxy-$C_1$-$C_4$-alkyl groups, and
P is a direct bond, a saturated or unsaturated carbon chain having 1 to 4 carbon atoms and optionally substituted by hydroxy groups, a carbonyl, sulfoxy, sulfonyl or imino group, an oxygen or sulfur atom, or a group with the formula III

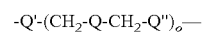

(III)

in which
Q is a direct bond, a CH$_2$ or CHOH group,
Q' and Q", independently of one another, are an oxygen atom, an NR$^{13}$ group, in which R$^{13}$ is a hydrogen atom, a $C_{1-4}$-alkyl or a hydroxy-$C_{1-4}$-alkyl group, it also being possible for the two groups, together with the remainder of the molecule, to form a 5-, 6- or 7-membered ring, the group O—(CH$_2$)$_p$—NH or NH—(CH$_2$)$_{p'}$—O, in which p and p' are 2 or 3, and
o is a number from 1 to 4, such as, for example, 4,4'-diaminostilbene and hydrochloride thereof, 4,4'-diaminostilbene-2,2'-disulfonic acid mono- or di-Na salt, 4-amino-4'-dimethylaminostilbene and hydrochloride thereof, 4,4'-diaminodiphenylmethane, 4,4'-diaminodiphenyl sulfide, 4,4'-diaminodiphenyl sulfoxide, 4,4'-diaminodiphenylamine, 4,4'-diaminodiphenylamine-2-sulfonic acid, 4,4'-diaminobenzophenone, 4,4'-diaminodiphenyl ether, 3,3',4,4'-tetraminodiphenyl, 3,3',4,4'-tetraminobenzophenone, 1,3-bis(2,4-diaminophenoxy)propane, 1,8-bis(2,5-diaminophenoxy)-3,6-dioxaoctane, 1,3-bis(4-aminophenylamino)propane, 1,3-bis(4-aminophenylamino)-2-propanol, 1,3-bis[N-(4-aminophenyl)-2-hydroxyethylamino]-2-propanol, N,N-bis[2-(4-aminophenoxy)ethyl]methylamine, N-phenyl-1,4-phenylenediamine and bis(5-amino-2-hydroxyphenyl)methane.

The above-mentioned compounds can be used either in free form or in the form of their physiologically compatible salts, in particular, as salts of inorganic acids, such as hydrochloric acid or sulfuric acid.

Suitable nitrogen-containing heterocyclic compounds are, for example, 2-aminopyridine, 3-aminopyridine, 4-aminopyridine, 2-amino-3-hydroxypyridine, 2,6-diaminopyridine, 2,5-diaminopyridine, 2-(aminoethylamino)-5-aminopyridine, 2,3-diaminopyridine, 2-dimethylamino-5-aminopyridine, 2-methylamino-3-amino-6-methoxypyridine, 2,3-diamino-6-methoxypyridine, 2,6-dimethoxy-3,5-diaminopyridine, 2,4,5-triaminopyridine, 2,6-dihydroxy-3,4-dimethylpyridine, N-[2-(2,4-diaminophenyl)aminoethyl]-N-(5-amino-2-pyridyl)amine, N-[2-(4-aminophenyl)aminoethyl]-N-(5-amino-2-pyridyl)amine, 2,4-dihydroxy-5,6-diaminopyrimidine, 4,5,6-triaminopyrimidine, 4-hydroxy-2,5,6-triaminopyrimidine, 2-hydroxy-4,5,6-triaminopyrimidine, 2,4,5,6-tetraminopyrimidine, 2-methylamino-4,5,6-triaminopyrimidine, 2,4-diaminopyrimidine, 4,5-diaminopyrimidine, 2-amino-4-methoxy-6-methylpyrimidine, 3,5-diaminopyrazole, 3,5-diamino-1,2,4-triazole, 3-aminopyrazole, 3-amino-5-hydroxypyrazole, 1-phenyl-4,5-diaminopyrazole, 1-(2-hydroxyethyl)-4,5-diaminopyrazole, 1-phenyl-3-methyl-4,5-diaminopyrazole, 4-amino-2,3-dimethyl-1-phenyl-3-pyrazolin-5-one (4-aminoantipyrine), 1-phenyl-3-methylpyrazol-5-one, 2-aminoquinoline, 3-aminoquinoline, 8-aminoquinoline, 4-aminoquinaldine, 2-aminonicotinic acid, 6-aminonicotinic acid, 5-aminoisoquinoline, 5-aminoindazole, 6-aminoindazole, 5-aminobenzimidazole, 7-aminobenzimidazole, 5-aminobenzothiazole, 7-aminobenzothiazole, 2,5-dihydroxy-4-morpholinoaniline, and indole and indoline derivatives, such as 4-aminoindole, 5-aminoindole, 6-aminoindole, 7-aminoindole, 5,6-dihydroxyindole, 5,6-dihydroxyindoline and 4-hydroxyindoline. Further heterocyclic compounds which can be used according to the invention are the hydroxypyrimidines disclosed in DE-U1-299 08 573. The above-mentioned compounds can be used either in free form or in the form of their physiologically compatible salts, e.g., as salts of inorganic acids, such as hydrochloric acid or sulfuric acid.

Suitable aromatic hydroxy compounds are, for example, 2-methylresorcinol, 4-methylresorcinol, 5-methylresorcinol, 2,5-dimethylresorcinol, resorcinol, 3-methoxyphenol, pyrocatechin, hydroquinone, pyrogallol, phloroglucine, hydroxyhydroquinone, 2-methoxyphenol, 3-methoxyphenol, 4-methoxyphenol, 3-dimethylaminophenol, 2-(2-hydroxyethyl)phenol, 3,4-methylenedioxyphenol, 2,4-dihydroxybenzoic acid, 3,4-dihydroxybenzoic acid, 2,4-dihydroxyphenylacetic acid, 3,4-dihydroxyphenylacetic acid, gallic acid, 2,4,6-trihydroxybenzoic acid, 2,4,6-trihydroxyacetophenone, 2-chlororesorcinol, 4-chlororesorcinol, 1-naphthol, 1,5-dihydroxynaphthalene, 2,3-dihydroxynaphthalene, 2,7-dihydroxynaphthalene, 6-dimethylamino-4-hydroxy-2-naphthalenesulfonic acid and 3,6-dihydroxy-2,7-naphthalenesulfonic acid.

The compounds of component A and the compounds of component B are preferably used in the compositions according to the invention in each case in an amount of from 0.03 to 65 mmol, in particular, from 1 to 40 mmol, based on 100 g of the overall dyeing composition. The molar ratio of the compound of component A and the compound of component B can be in the range from 0.5 to 2.0, preference being given to using equimolar amounts. If components A and B are stored separately, the actual dyeing composition is prepared directly prior to use by mixing.

An oxidative coloration of the fibers can take place in the presence of oxidation dye precursors in principle with atmospheric oxygen. However, it is preferred to use a chemical oxidizing agent, particularly when a lightening effect of the natural pigments of human hair besides the coloring is desired. This lightening effect may be desired independently of the dyeing method. The presence of oxidation dye precursors is accordingly not a necessary prerequisite for the use of oxidizing agents in the dyeing compositions of the method according to the invention. Suitable oxidizing agents are, in particular, hydrogen peroxide and its addition products onto urea, melamine and sodium borate. If the dye precursors and the oxidizing agent are stored separately, the actual dyeing composition is prepared directly prior to use by mixing.

According to the invention, it is preferred to formulate the dyeing compositions of the method according to the invention to be free from peroxo compounds. Peroxo compounds are defined as the compounds as are described below in the scope of the preferred embodiments of the nuancing agent.

According to the invention, however, the oxidation dyeing composition can also be applied to the hair together with a catalyst which activates the oxidation of the dye precursors, e.g., by atmospheric oxygen. Such catalysts are, for example, metal ions, iodides, quinones or certain enzymes.

Suitable metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. Of particular suitability in this connection are $Zn^{2+}$, $Cu^{2+}$ and $Mn^{2+}$. The metal ions can in principle be used in the form of any physiologically compatible salt or in the form of a complex compound. Preferred salts are the acetates, sulfates, halides, lactates and tartrates. The use of these metal salts can both accelerate the development of the coloration and also influence the color nuance in a targeted manner.

Suitable enzymes are, for example, peroxidases, which can considerably enhance the effect of small amounts of hydrogen peroxide. Also of suitability according to the invention are those enzymes which directly oxidize the oxidation dye precursors with the help of atmospheric oxygen, such as, for example, the laccases, or produce in situ small amounts of hydrogen peroxide and in so doing biocatalytically activate the oxidation of the dye precursors. Particularly suitable catalysts for the oxidation of the dye precursors are the so-called 2-electron oxidoreductases in combination with the substrates specific therefor, e.g., pyranose oxidase and, e.g., D-glucose or galactose,
  glucose oxidase and D-glucose,
  glycerol oxidase and glycerol,
  pyruvate oxidase and pyruvic acid or salts thereof,
  alcohol oxidase and alcohol (MeOH, EtOH),
  lactate oxidase and lactic acid and salts thereof,
  tyrosinase oxidase and tyrosine,
  uricase and uric acid or salts thereof,
  choline oxidase and choline,
  amino acid oxidase and amino acids.

When using oxidizing agents, the actual dyeing composition is expediently prepared directly prior to use by mixing the preparation of the oxidizing agent with the preparation comprising the compounds of the formula I and optionally dye precursors. The ready-to-use hair dyeing preparation prepared in this way should preferably have a pH in the range from 6 to 12. Particular preference is given to using the hair dyeing composition in a weakly alkaline medium. The application temperatures can be in a range between 15 and 40° C. After a contact time of from 5 to 45 minutes, the hair dyeing composition is removed from the hair to be dyed by rinsing. After-washing with a shampoo is omitted if a heavily surfactant-laden carrier, e.g., a coloring shampoo, has been used.

Particularly in the case of hair which is difficult to dye, it is possible to apply a composition according to the invention to the hair optionally with additional dye precursors but also without prior mixing with the oxidizing component. After a contact time of from 20 to 30 minutes and—optionally following interim rinsing—the oxidizing component is then applied. After a further contact time of from 10 to 20 minutes, the hair is then rinsed and, if desired, after-shampooed. In this embodiment, according to a first variant in which the prior application of the dye precursors should bring about better penetration into the hair, the corresponding composition is adjusted to a pH of from about 4 to 7. According to a second variant, an air oxidation is firstly desired, in which case the applied composition preferably has a pH of from 7 to 10. During the subsequent accelerated after-oxidation, the use of peroxydisulfate solutions which have been rendered acidic as oxidizing agent may be preferred.

The compositions of the method according to the invention comprise the ingredients according to the invention preferably in a suitable aqueous, alcoholic or aqueous-alcoholic cosmetic carrier. Such carriers are, for example, creams, emulsions, gels and also surfactant-containing foaming solutions, such as, for example, shampoos, foam aerosols or other preparations which are suitable for use on the hair. However, it is also conceivable to integrate the ingredients into a pulverulent or tablet-like formulation.

For the purposes of the present invention, aqueous-alcoholic solutions are understood as meaning aqueous solutions comprising 3 to 70% by weight of a $C_1$-$C_4$-alcohol, in particular, ethanol or isopropanol. The compositions according to the invention can additionally comprise further organic solvents, such as, for example, methoxybutanol, benzyl alcohol, ethyl diglycol or 1,2-propylene glycol. Preference here is given to all water-soluble organic solvents.

The dyeing compositions and the nuancing agents of the method according to the invention can also comprise all active ingredients, additives and auxiliaries known for such preparations.

In many cases, the dyeing compositions and/or the nuancing agents comprise at least one surfactant, with both anionic and also zwitterionic, ampholytic, nonionic and cationic surfactants being suitable in principle. In many cases, however, it has proven advantageous to choose the surfactants from anionic, zwitterionic or nonionic surfactants.

Suitable anionic surfactants in preparations according to the invention are all anionic surface-active substances suitable for use on the human body. These are characterized by a water-solubilizing anionic group such as, for example, a carboxylate, sulfate, sulfonate or phosphate group, and a lipophilic alkyl group having about 10 to 22 carbon atoms. In addition, glycol or polyglycol ether groups, ester groups, ether groups and amide groups and also hydroxyl groups, may be present in the molecule. Examples of suitable anionic surfactants are, in each case in the form of the sodium, potassium and ammonium and also the mono-, di- and trialkanolammonium salts having 2 or 3 carbon atoms in the alkanol group, linear fatty acids having 10 to 22 carbon atoms (soaps),
ether carboxylic acids of the formula R—O—($CH_2$—$CH_2O$)$_x$—$CH_2$—COOH, in which R is a linear alkyl group having 10 to 22 carbon atoms and x=0 or 1 to 16,
acyl sarcosides having 10 to 18 carbon atoms in the acyl group,
acyl taurides having 10 to 18 carbon atoms in the acyl group,
acyl isethionates having 10 to 18 carbon atoms in the acyl group,
sulfosuccinic mono- and dialkyl esters having 8 to 18 carbon atoms in the alkyl group and sulfosuccinic monoalkylpolyoxyethyl esters having 8 to 18 carbon atoms in the alkyl group and 1 to 6 oxyethyl groups,
linear alkanesulfonates having 12 to 18 carbon atoms,
linear alpha-olefinsulfonates having 12 to 18 carbon atoms,
alpha-sulfo fatty acid methyl esters of fatty acids having 12 to 18 carbon atoms,
alkyl sulfates and alkylpolyglycol ether sulfates of the formula R—O—($CH_2$—$CH_2O$)$_x$—$SO_3H$, in which R is a preferably linear alkyl group having 10 to 18 carbon atoms and x=0 or 1 to 12,
mixtures of surface-active hydroxysulfonates according to DE-A-37 25 030,
sulfated hydroxyalkyl polyethylene and/or hydroxyalkylene propylene glycol ethers according to DE-A-37 23 354,
sulfonates of unsaturated fatty acids having 12 to 24 carbon atoms and 1 to 6 double bonds according to DE-A-39 26 344,
esters of tartaric acid and citric acid with alcohols, which constitute addition products of about 2-15 molecules of ethylene oxide and/or propylene oxide onto fatty alcohols having 8 to 22 carbon atoms.

Preferred anionic surfactants are alkyl sulfates, alkylpolyglycol ether sulfates and ether carboxylic acids having 10 to 18 carbon atoms in the alkyl group and up to 12 glycol ether groups in the molecule, and in particular, salts of saturated and in particular, unsaturated $C_8$-$C_{22}$-carboxylic acids, such as oleic acid, stearic acid, isostearic acid and palmitic acid.

Nonionogenic surfactants comprise, as hydrophilic group, e.g., a polyol group, a polyalkylene glycol ether group or a combination of polyol and polyglycol ether group. Such compounds are, for example, addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group,
$C_{12}$-$C_{22}$-fatty acid mono- and diesters of addition products of from 1 to 30 mol of ethylene oxide onto glycerol,
$C_8$-$C_{22}$-alkylmono- and oligoglycosides and ethoxylated analogs thereof, and
addition products of from 5 to 60 mol of ethylene oxide onto castor oil and hydrogenated castor oil.

Preferred nonionic surfactants are alkyl polyglycosides of the general formula $R^1$O-$(Z)_x$. These compounds are characterized by the following parameters.

The alkyl radical $R^1$ comprises 6 to 22 carbon atoms and can either be linear or branched. Preference is given to primary linear and 2-position methyl-branched aliphatic radicals. Such alkyl radicals are, for example, 1-octyl, 1-decyl, 1-lauryl, 1-myristyl, 1-cetyl and 1-stearyl. Particular preference is given to 1-octyl, 1-decyl, 1-lauryl, 1-myristyl. If so-called oxo alcohols are used as starting materials, compounds with an uneven number of carbon atoms in the alkyl chain predominate.

The alkyl polyglycosides which can be used according to the invention can comprise, for example, only a specific alkyl radical $R^1$. Usually, these compounds, however, are prepared starting from natural fats and oils or mineral oils. In this case, the alkyl radicals R present are mixtures corresponding to the starting compounds or corresponding to the particular workup of these compounds.

Particular preference is given to those alkyl polyglycosides in which $R^1$ consists
- essentially of $C_8$— and $C_{10}$-alkyl groups,
- essentially of $C_{12}$— and $C_{14}$-alkyl groups,
- essentially of $C_8$-$C_{16}$-alkyl groups or
- essentially of $C_{12}$-$C_{16}$-alkyl groups.

The sugar building block Z which may be used is any mono- or oligosaccharides. Usually, sugars with 5 or 6 carbon atoms, and the corresponding oligosaccharides are used. Such sugars are, for example, glucose, fructose, galactose, arabinose, ribose, xylose, lyxose, allose, altrose, mannose, gulose, idose, talose and sucrose. Preferred sugar building blocks are glucose, fructose, galactose, arabinose and sucrose; glucose is particularly preferred.

The alkyl polyglycosides which can be used according to the invention comprise, on average, 1.1 to 5 sugar units. Alkyl polyglycosides with x values of from 1.1 to 1.6 are preferred. Very particular preference is given to alkyl glycosides in which x is 1.1 to 1.4.

Besides their surfactant effect, the alkyl glycosides also serve to improve the fixing of scent components on the hair. Thus, when it is desirable for the effect of the perfume oil on the hair to last beyond the hair treatment, the person skilled in the art will preferably have recourse to this class of substances as a further ingredient of the preparations according to the invention.

The alkoxylated homologs of the specified alkyl polyglycosides can also be used according to the invention. These homologs can, on average, comprise up to 10 ethylene oxide and/or propylene oxide units per alkyl glycoside unit.

It is also possible to use zwitterionic surfactants, in particular, as cosurfactants. Zwitterionic surfactants is the term used for those surface-active compounds which carry at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethylammonium glycinates, for example, cocoalkyldimethylammonium glycinate, N-acylaminopropyl-N,N-dimethylammonium glycinates, for example, cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethyl hydroxyethylcarboxymethyl glycinate. A preferred zwitterionic surfactant is the fatty acid amide derivative known under the INCI name Cocamidopropyl Betaine.

Likewise suitable in particular, as cosurfactants are ampholytic surfactants. Ampholytic surfactants are understood as meaning those surface-active compounds which, apart from a $C_8$-$C_{18}$-alkyl or acyl group in the molecule, comprise at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12-18}$-acylsarcosine.

The cationic surfactants used according to the invention are, in particular, those of the quaternary ammonium compound type, the ester quat type and the amidoamine type.

Preferred quaternary ammonium compounds are ammonium halides, in particular, chlorides and bromides, such as alkyltrimethylammonium chlorides, dialkyldimethylammonium chlorides and trialkylmethylammonium chlorides, e.g., cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, and the imidazolium compounds known under the INCI names Quaternium-27 and Quaternium-83. The long alkyl chains of the above-mentioned surfactants preferably have 10 to 18 carbon atoms.

Ester quats are known substances which comprise both at least one ester function and also at least one quaternary ammonium group as structural element. Preferred ester quats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold, for example, under the trade names Stepantex®, Dehyquart® and Armocare®. The products Armocare® VGH-70, an N,N-bis(2-palmitoyloxyethyl)dimethylammonium chloride, and Dehyquart® F-75 and Dehyquart® AU-35 are examples of such ester quats.

The alkylamidoamines are usually prepared by amidation of natural or synthetic fatty acids and fatty acid cuts with dialkylaminoamines. A compound particularly suitable according to the invention from this group of substances is the stearamidopropyldimethylamine commercially available under the name Tegoamid® S 18.

Further cationic surfactants which can be used according to the invention are the quaternized protein hydrolyzates.

Likewise suitable according to the invention are cationic silicone oils, such as, for example, the commercially available products Q2-7224 (manufacturer: Dow Corning; a stabilized trimethylsilylamodimethicone), Dow Corning 929 emulsion (comprising a hydroxyamino-modified silicone, which is also referred to as amodimethicone), SM-2059 (manufacturer: General Electric), SLM-55067 (manufacturer: Wacker), and Abil®-Quat 3270 and 3272 (manufacturer: Th. Goldschmidt; diquaternary polydimethylsiloxanes, Quaternium-80).

One example of a quaternary sugar derivative which can be used as cationic surfactant is the commercial product Glucquat® 100, according to INCI nomenclature a "Lauryl Methyl Gluceth-10 Hydroxypropyl Dimonium Chloride".

The compounds with alkyl groups used as surfactant may in each case be uniform substances. However, it is usually preferred when producing these substances to start from native vegetable or animal raw materials, thus giving rise to mixtures of substances with varying alkyl chain lengths dependent on the particular raw material.

In the case of the surfactants which constitute addition products of ethylene oxide and/or propylene oxide onto fatty alcohols or derivatives of these addition products it is possible to use either products with a "normal" homolog distribution or those with a narrowed homolog distribution. In this connection, "normal" homolog distribution is understood as meaning mixtures of homologs which are obtained during the reaction of fatty alcohol and alkylene oxide using alkali metals, alkali metal hydroxides or alkali metal alkoxides as catalysts. Narrowed homolog distributions are, by contrast, obtained if, for example, hydrotalcites, alkaline earth metal salts of ether carboxylic acids, alkaline earth metal oxides, hydroxides or alkoxides are used as catalysts. The use of products with a narrowed homolog distribution may be preferred.

In addition, the dyeing compositions and the nuancing agents according to the invention can comprise further active ingredients, auxiliaries and additives, such as, for example,
- nonionic polymers, such as, for example, vinylpyrrolidone/vinyl acrylate copolymers, polyvinylpyrrolidone and vinylpyrrolidone/vinyl acetate copolymers and polysiloxanes,
- cationic polymers, such as quaternized cellulose ethers, polysiloxanes with quaternary groups, dimethyldiallylammonium chloride polymers, acrylamide-dimethyldiallylammonium chloride copolymers, dimethylaminoethyl methacrylate-vinylpyrrolidone copolymers quaternized with diethyl sulfate, vinylpyrrolidone-imidazolinium methochloride copolymers and quaternized polyvinyl alcohol,
- zwitterionic and amphoteric polymers, such as, for example, acrylamidopropyltrimethylammonium chloride/acrylate copolymers and octylacrylamide/methyl methacrylate/tert-butylaminoethyl methacrylate/2-hydroxypropyl methacrylate copolymers,
- anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers,
- structurants, such as maleic acid and lactic acid,
- hair-conditioning compounds, such as phospholipids, for example, soya lecithin, egg lecithin and cephalins,
- protein hydrolyzates, in particular, elastin, collagen, keratin, milk protein, soya protein and wheat protein hydrolyzates, their condensation products with fatty acids, and quaternized protein hydrolyzates,
- perfume oils, dimethyl isosorbide and cyclodextrins,
- solvents and solubility promoters, such as ethanol, isopropanol, ethylene glycol, propylene glycol, glycerol and diethylene glycol,
- fiber-structure-improving active ingredients, in particular, mono-, di- and oligosaccharides, such as, for example, glucose, galactose, fructose, fruit sugars and lactose,
- quaternized amines, such as methyl-1-alkylamidoethyl-2-alkylimidazolinium methosulfate
- antifoams, such as silicones,
- dyes for coloring the composition,
- antidandruff active ingredients, such as piroctone olamine, zinc omadine and climbazole,
- photoprotective agents, in particular, derivatized benzophenones, cinnamic acid derivatives and triazines,
- substances for adjusting the pH, such as, for example, customary acids, in particular, food acids and bases,
- active ingredients, such as allantoin, pyrrolidonecarboxylic acids and salts thereof, and bisabolol,
- vitamins, provitamins and vitamin precursors, in particular, those of groups A, $B_3$, $B_5$, $B_6$, C, E, F and H,
- plant extracts, such as the extracts from green tea, oak bark, stinging nettle, hamamelis, hops, camomile, burdock, horsetail, hawthorn, linden blossom, almond, aloe vera, fir needle, roast chestnut, sandalwood, juniper, coconut, mango, apricot, lemon, wheat, kiwi, melon, orange, grapefruit, sage, rosemary, birch, mallow, lady's smock, wild thyme, yarrow, thyme, melissa, restharrow, coltsfoot, marshmallow, meristem, ginseng and ginger root,
- cholesterol,
- consistency regulators, such as sugar esters, polyol esters and polyol alkyl ethers,
- fats and waxes, such as spermaceti, beeswax, montan wax and paraffins,
- fatty acid alkanolamides,
- complexing agents, such as EDTA, NTA, β-alaninediacetic acid and phosphonic acids,
- swelling and penetration substances, such as glycerol, propylene glycol monoethyl ether, carbonates, hydrogencarbonates, guanidines, ureas, and primary, secondary and tertiary phosphates,
- opacifiers, such as latex, styrene/PVP and styrene/acrylamide copolymers
- pearlizing agents, such as ethylene glycol mono- and distearate, and PEG-3 distearate,
- pigments,
- stabilizers for hydrogen peroxide and other oxidizing agents,
- propellants, such as propane-butane mixtures, $N_2O$, dimethyl ether, $CO_2$ and air,
- antioxidants.

With regard to further optional components and to the amounts of these components used, reference is made expressly to the relevant handbooks known to the person skilled in the art, e.g., Kh. Schrader, Grundlagen und Rezepturen der Kosmetika [Fundamentals and formulations of cosmetics], 2nd edition, Hüthig Buch Verlag, Heidelberg, 1989.

The application temperatures of the dyeing composition can be in a range between 15 and 40° C. After a contact time Z1 of preferably 2 to 60 minutes, particularly preferably from 5 to 45 minutes, the hair dyeing composition is removed from the hair to be dyed by rinsing. After-washing with a shampoo is omitted if a heavily surfactant-laden carrier, e.g., a coloring shampoo, has been used.

It is essential to the invention to carry out the nuancing step C of the method according to the invention directly after step A and/or step B. The time which is defined as directly afterwards for the purposes of the invention is at most 90 minutes. The preferred time interval between the completed procedure of step A of the method according to the invention and the start of the procedure of step C should be not longer than 60 minutes, particularly preferably not longer than 45 minutes, very particularly preferably not longer than 20 minutes.

The contrast transition between the dyed areas of hair and the oxidatively lightened areas of hair is more marked if the hair is dried between step A and C and the nuancing agent is applied to the dry hair.

The nuancing agent is applied to part of the keratin-containing fibers dyed previously in step A. This means that one or more partial amounts are chosen from the quantity of dyed fibers as fiber bundles. These fiber bundles, if they are human hair, should be chosen to achieve uniformly distributed color effects, not only on the covering hair, but also on the areas of hair which lie underneath the covering hair. In addition, the chosen fiber bundles are preferably selected as uniformly as possible over the area of the entire head hair area. The chosen fiber bundles are treated either completely or partially with the nuancing agent. In the case of complete treatment, strands are obtained with light color effects. In the case of partial treatment, the fiber ends or other selected areas of the fiber bundle, for example, can be selectively nuanced.

The nuancing agent can in principle be applied to the selected fiber strands by hand using appropriate protective gloves. However, the nuancing agent is preferably applied to the areas of hair intended for nuancing using an applicator, such as, for example, brushes or an applicette. An applicette is understood as meaning a broad brush at whose handle end there is a point which permits and simplifies the separation of fiber bundles or strands from the entirety of the fibers.

It is preferred, particularly when carrying out the nuancing on short hair up to 20 cm in length or for nuancing hair ends, to use a round brush as applicator. A round brush has a handle and a bristle head. The bristles of the bristle head in the case of a round brush are arranged in the form of a cylinder around a central body of the bristle head, the totality of the attached bristles at one bristle end describing an essentially cylindrical outer surface while at the other end it is attached to the body of the bristle head. The body of the bristle head is in turn positioned at the end of the round brush construction or is part of an end area of the construction. The round brush used in the method according to the invention preferably has bristles which are at most 2 cm in length and has a diameter for the cylindrical bristle head of at most 2.5 cm. The cylinder of the bristle head has a length of at most 4 cm. To apply the nuancing agent, a mascara brush is exceptionally suitable.

A particularly preferred way of achieving an improved uniform application of the nuancing agent for the application of color effects in the form of strands over the head hair area while retaining sharp contrasts is to use a cap having a plurality of markings for the placement of holes in the surface of the cap arranged in a grid-like pattern spread over the surface of the cap. In another embodiment of the cap, the cap surface can also have a plurality of pre-formed holes instead of markings for holes. In a preferred embodiment of the method, the preferably dry fibers after step B or step (C) are therefore covered with such a cap. Using an aid in the form of a crochet hook, fiber bundles or hair strands are then pulled through holes in the cap. These holes can be pre-formed or made by penetrating the cap at the positions of the markings. Subsequently, using suitable protective gloves, the nuancing agent according to step C is then distributed onto the selected areas of hair by hand as in the case of a shampoo or using a brush. After a contact time Z2, the nuancing agent is rinsed off and the cap is removed.

The cap is preferably made from at least one film which preferably consists of polyethylene or polyvinyl chloride. If the cap consists of one film layer, it is possible to prestamp or predraw the plurality of holes arranged in a grid-like pattern. In the case of a merely predrawn pattern, the film has no holes and has to be punctured at the selected predrawn place and the hair strands are then pulled through the hole thus formed. It is preferred according to the invention to make the cap from two superimposed film layers. These film layers preferably consist of polyethylene or polyvinyl chloride. The film on the inside of the cap preferably has no premade holes. In addition, the outer film bears the preferably already prepunched grid-like pattern.

The holes in the hole grid and their predrawing preferably have a diameter of from 0.1 to 0.75 mm. The optionally only predrawn holes are preferably arranged such that they lie on the imaginary lines of a grid. The grid preferably consists of quadrants. All optionally only predrawn holes have a uniform distance along the grid lines; this is preferably 0.5 to 2 cm.

Figure 2:
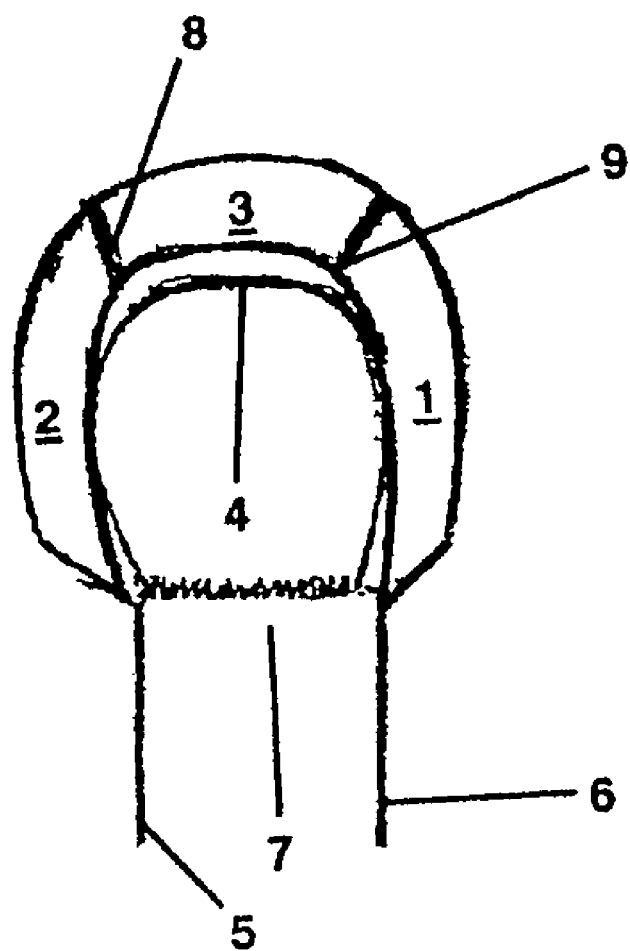
FIG. 2. Depicts a front view of a cap according to the invention.
Figure 3:
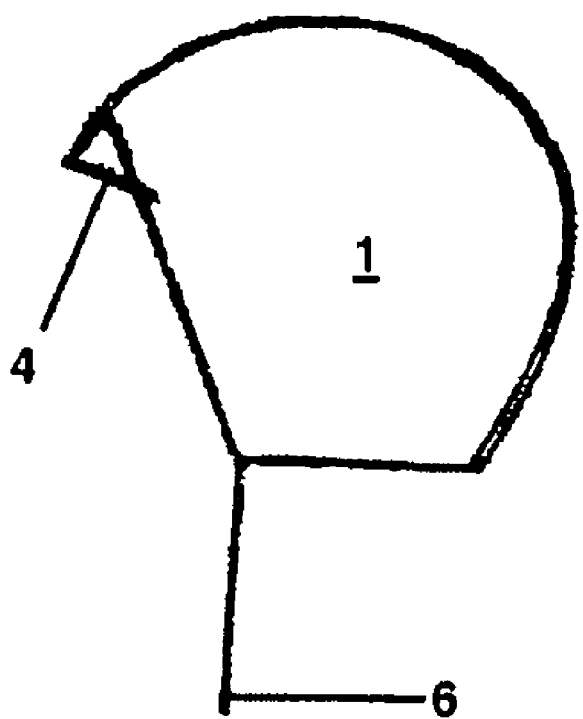
FIG. 3. Depicts a full side view of a cap according to the invention.
Figure 4:
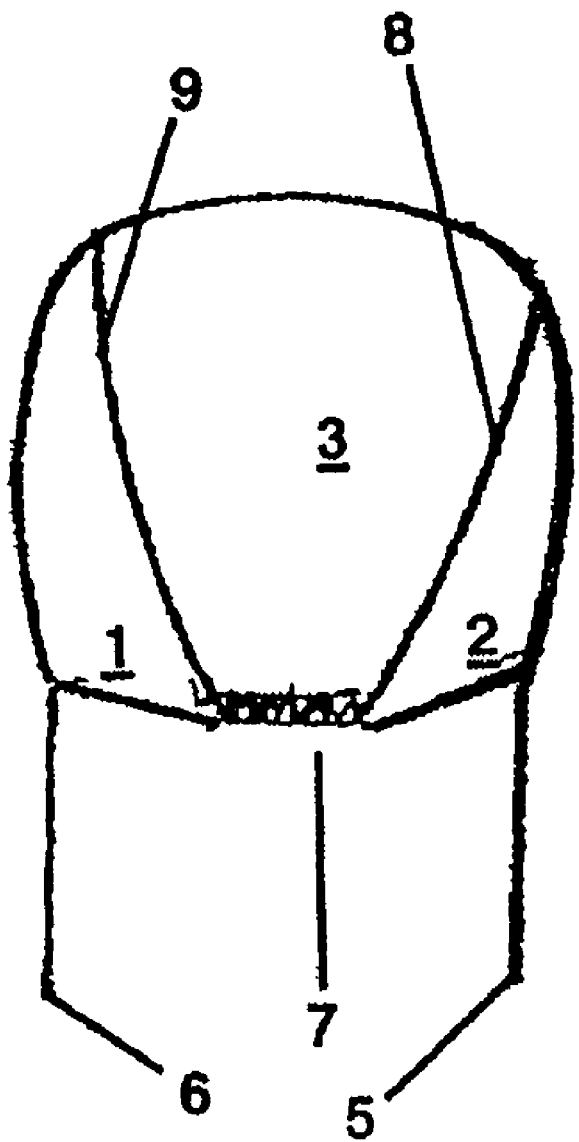
FIG. 4. Depicts a rear view of a cap according to the invention.

The cap is preferably in the shape of a boat or a helmet. Particular preference is given to the helmet form. Very particular preference is given to a cap as is depicted in FIGS. 1 to 4. This cap consists primarily of two side sections (1) and (2) and a middle section (3) and a peaked section (4). These sections are joined together at their contact points preferably through a sealed and/or sewn seam (8) and (9). The seams and the outer edges of sections (1), (2), (3) and (4) are edged with a hem. The hem preferably consists of the material of the outer film. The sections (1), (2) and (3) of the cap consist of 2 superimposed films. The outer film has a prepunched hole grid, the inner film has no holes. The two superimposed films are joined together firstly by the joining seam of sections (1), (2) and (3), and secondly by the hem. When pulled over the head, the cap covers the back of the head and has an opening at the front for the face (see FIG. 2, the "front view"). The peaked section (4) is attached to the upper section of the face area. The edge of the peaked section and the outer edge of sections (1), (2) and (3) are edged as described above by a hem. The hem is extended in the lower region of the face area beyond the edge of the cap and forms the tapes (5) and (6) right and left, with which the cap can be secured on the head by tying the tapes under the chin. FIG. 2 and FIG. 4 show the piece of elastic (7) which is incorporated along the lower edge of the middle section (3). The piece of elastic ensures that the cap is close-fitting. Using the piece of elastic, the cap can be adapted to different head sizes.

The contact time Z2 is preferably 5 to 60 minutes, particularly preferably 20 to 45 minutes.

In another embodiment of the method, the fiber bundles which have been separated off and treated with the nuancing agent are wrapped in a foil, preferably in aluminum foil, and left in this foil for the duration of the contact time Z2. This embodiment can preferably be used for shorter contact times of up to 30 minutes.

The nuancing agents of the method according to the invention comprise hydrogen peroxide. The hydrogen peroxide is added to the nuancing agent as a solution or in the form of a solid addition compound of hydrogen peroxide onto inorganic or organic compounds, such as, for example, sodium perborate, sodium percarbonate, magnesium percarbonate, sodium percarbamide, polyvinylpyrrolidone.n $H_2O_2$ (n is a positive integer greater than 0), urea peroxide and melamine peroxide. Hydrogen peroxide is preferably present in the nuancing agents in an amount of from 0.5 to 6.0% by weight, based on the weight of the nuancing agent.

The nuancing agents of the method according to the invention preferably comprise additional peroxo compounds. These are understood as meaning those peroxo compounds which represent neither hydrogen peroxide itself, nor addition products of hydrogen peroxide onto other components. The selection of the peroxo compounds additionally present in the compositions according to the invention is not in principle subject to any limitations; customary peroxo compounds known to the person skilled in the art are, for example, ammonium peroxydisulfate, potassium peroxydisulfate, sodium peroxydisulfate, ammonium persulfate, potassium persulfate, sodium persulfate, potassium peroxydiphosphate and peroxides such as magnesium and barium peroxide. Among these peroxo compounds, which can also be used in combination, the inorganic compounds are preferred according to the invention. Particular preference is given to the peroxydisulfates, in particular, ammonium peroxydisulfate.

The peroxo compounds are present in the nuancing agents used according to the invention preferably in amounts of from 1 to 40% by weight, in particular, in amounts of from 2 to 30% by weight.

The pH of the nuancing agents used according to the invention is preferably in a pH range from pH 2.5 to 12.0, particularly preferably from pH 8.5 to 11.0.

The nuancing agents of the method according to the invention comprise, as preferred alkalanizing agent, at least one compound chosen from ammonium, alkali metal and alkaline earth metal hydroxides, carbonates, hydrogencarbonates, hydroxycarbonates and carbamides, and also alkali metal phosphates.

In addition, the nuancing agent can additionally comprise at least one $SiO_2$ compound, which may be optionally hydrated. According to the invention, it may be preferred to use the optionally hydrated $SiO_2$ compounds in amounts of from 0.05% by weight to 15% by weight, particularly preferably in amounts of from 0.15% by weight to 10% by weight and very particularly preferably in amounts of from 0.2% by weight to 5% by weight, in each case based on the overall nuancing agent. The quantitative data here in each case give the content of the $SiO_2$ compounds (without their water fraction) in the agents.

With regard to the optionally hydrated $SiO_2$ compounds, the present invention is not in principle subject to any limitations. Preference is given to silicic acids, their oligomers and polymers, and their salts. Preferred salts are the alkali metal salts, in particular, the potassium and sodium salts. The sodium salts are very particularly preferred.

The optionally hydrated $SiO_2$ compounds can be present in various forms. According to the invention, the $SiO_2$ compounds are preferably used in the form of silica gels or particularly preferably as waterglass. Some of these $SiO_2$ compounds may be in the form of an aqueous solution.

According to the invention, very particular preference is given to waterglasses which are formed from a silicate of the formula $(SiO_2)_n(Na_2O)_m(K_2O)_p$, where n is a positive rational number and m and p, independently of one another, are a positive rational number or are 0, with the provisos that at least one of the parameters m or p is different from 0 and the ratio between n and the sum of m and p is between 1:4 and 4:1.

Besides the components described by the empirical formula, the waterglasses can also comprise, in small amounts, further additives, such as, for example, phosphates or magnesium salts.

Waterglasses of particular preference according to the invention are sold, interalia, by Henkel under the names Ferrosil® 119, soda waterglass 40/42, Portil® A, Portil® AW, Portil® N and Portil® W, and by Akzo under the name Britesil® C20.

The nuancing agent has a preferred viscosity of from 5,000 to 100,000 mPa·s, particularly preferably from 30,000 to 80,000 mPa·s (Brookfield rotary viscometer, 25° C., spindle #4, 20 rpm).

The viscosity is adjusted through the thickener present in the nuancing agent. Polymers can increase the viscosity of aqueous and nonaqueous phases in cosmetic preparations. In aqueous phases, their function increasing the viscosity is based on their solubility in water or their hydrophilic nature. They are used both in surface-active and also in emulsion-like systems. Some examples of preferred polymeric thickeners are listed below; these may be present in the nuancing agent of the method according to the invention: Acrylamide Copolymers, Acrylamide/Sodium Acrylate Copolymer, Acrylamide/Sodium Acryloyldimethyltaurate Copolymer, Acrylates/Acetoacetoxyethyl Methacrylate Copolymer, Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Crosspolymer, Acrylic Acid/Acrylonitrogens Copolymer, Agar, Agarose, *Alcaligenes* Polysaccharides, Algin, Alginic Acid, Ammonium Acrylates/Acrylonitrogens Copolymer, Ammonium Acrylates Copolymer, Ammonium Acryloyldimethyltaurate/Vinyl Formamide Copolymer, Ammonium Acryloyldimethyltaurate/VP Copolymer, Ammonium Alginate, Ammonium Polyacryloyldimethyl Taurate, Amylopectin, Ascorbyl Methylsilanol Pectinate, *Astragalus* Gummifer Gum, Attapulgite, *Avena Sativa* (Oat), Kernel Flour, Bentonite, Butoxy Chitosan, Caesalpinia Spinosa Gum, Calcium Alginate, Calcium Carboxymethyl Cellulose, Calcium Carrageenan, Calcium Potassium Carbomer, Calcium Starch Octenylsuccinate, C20-40 Alkyl Stearate, Carbomer, Carboxybutyl Chitosan, Carboxymethyl Chitin, Carboxymethyl Chitosan, Carboxymethyl Dextran, Carboxymethyl Hydroxyethylcellulose, Carboxymethyl Hydroxypropyl Guar, Cellulose Acetate Propionate Carboxylate, Cellulose Gum, Ceratonia Siliqua Gum, Cetyl Hydroxyethylcellulose, Cholesterol/HDI/Pullulan Copolymer, Cholesteryl Hexyl Dicarbamate Pullulan, *Cyamopsis Tetragonoloba* (Guar) Gum, Diglycol/CHDM/Isophthalates/SIP Copolymer, Dihydrogenated Tallow Benzylmonium Hectorite, Dimethicone Crosspolymer-2, Dimethicone Propyl PG-Betaine, DMAPA Acrylates/Acrylic Acid/Acrylonitrogens Copolymer, Ethylene/Sodium Acrylate Copolymer, Gelatin, Gellan Gum, Glyceryl Alginate, *Glycine* Soja (Soybean) Flour, Guar Hydroxypropyltrimonium Chloride, Hectorite, Hydrated Silica, Hydrogenated Potato Starch, Hydroxybutyl, Methylcellulose, Hydroxyethyl Acrylate/Sodium Acryloyldimethyl Taurate Copolymer, Hydroxyethylcellulose, Hydroxyethyl Chitosan, Hydroxyethyl Ethylcellulose, Hydroxypropylcellulose, Hydroxypropyl Chitosan, Hydroxypropyl Ethylenediamine Carbomer, Hydroxypropyl Guar, Hydroxypropyl Methylcellulose, Hydroxypropyl Methylcellulose Stearoxy Ether, Hydroxypropyl Starch, Hydroxypropyl Starch Phosphate, Hydroxypropyl Xanthan Gum, Hydroxystearamide MEA, Isobutylene/Sodium Maleate Copolymer, Lithium Magnesium Silicate, Lithium Magnesium Sodium Silicate, Macrocystis Pyrifera (Kelp), Magnesium Alginate, Magnesium Aluminum Silicate, Magnesium Silicate, Magnesium Trisilicate, Methoxy PEG-22/Dodecyl Glycol Copolymer, Methylcellulose, Methyl Ethylcellulose, Methyl Hydroxyethylcellulose, Microcrystalline Cellulose, Montmorillonite, Moroccan Lava Clay, Natto Gum, Nonoxynyl Hydroxyethylcellulose, Octadecene/MA Copolymer, Pectin, PEG-800, PEG-Crosspolymer, PEG-150/Decyl Alcohol/SMDI Copolymer, PEG-175 Diisostearate, PEG-190 Distearate, PEG-15 Glyceryl Tristearate, PEG-140 Glyceryl Tristearate, PEG-240/HDI Copolymer Bis-Decyltetradeceth-20 Ether, PEG-100/IPDI Copolymer, PEG-180/Laureth-50/TMMG Copolymer, PEG-10/Lauryl Dimethicone Crosspolymer, PEG-15/Lauryl Dimethicone Crosspolymer, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, PEG-120 Methyl Glucose Trioleate, PEG-180/Octoxynol-40/TMMG Copolymer, PEG-150 Pentaerythrityl Tetrastearate, PEG-4 Rapeseedamide, PEG-150/Stearyl Alcohol/SMDI Copolymer, Polyacrylate-3, Polyacrylic Acid, Polycyclopentadiene, Polyether-1, Polyethylene/Isopropyl Maleate/MA Copolyol, Polymethacrylic Acid, Polyquaternium-52, Polyvinyl Alcohol, Potassium Alginate, Potassium Aluminum Polyacrylate, Potassium Carbomer, Potassium Carrageenan, Potassium Polyacrylate, Potato Starch Modified, PPG-14 Laureth-60 Hexyl Dicarbamate, PPG-14 Laureth-60 Isophoryl Dicarbamate, PPG-14 Palmeth-60 Hexyl Dicarbamate Propylene Glycol Alginate, PVP/Decene Copolymer, PVP Montmorillonite, Rhizobian Gum, Ricinoleic Acid/Adipic Acid/AEEA Copolymer, Sclerotium Gum, Sodium Acrylate/Acryloyldimethyl Taurate Copolymer, Sodium Acrylates/Acrolein Copolymer, Sodium Acrylates/ Acrylonitrogens Copolymer, Sodium Acrylates Copolymer, Sodium AcrylatesNinyl Isodecanoate Crosspolymer, Sodium AcrylateNinyl Alcohol Copolymer, Sodium Carbomer, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Cyclodextrin Sulfate, Sodium Hydroxypropyl Starch Phosphate, Sodium Isooctylene/MA Copolymer, Sodium Magnesium Fluorosilicate, Sodium Polyacrylate, Sodium Polyacrylate Starch, Sodium Polyacryloyldimethyl Taurate, Sodium Polymethacrylate, Sodium Polystyrene Sulfonate, Sodium Silicoaluminate, Sodium Starch Octenylsuccinate, Sodium Stearoxy, PG-Hydroxyethylcellulose Sulfonate, Sodium Styrene/Acrylates Copolymer, Sodium Tauride Acrylates/Acrylic Acid/Acrylonitrogens Copolymer, *Solanum Tuberosum* (Potato) Starch, Starch/Acrylates/Acrylamide Copolymer, Starch Hydroxypropyltrimonium Chloride, Steareth-60 Cetyl Ether, Steareth-100/PEG-136/HDI Copolymer, Sterculia Urens Gum, Synthetic Fluorphlogopite, Tamarindus Indica Seed Gum, Tapioca Starch, TEA-Alginate, TEA-Carbomer, *Triticum Vulgare* (Wheat) Starch, Tromethamine Acrylates/Acrylonitrogens Copolymer, Tromethamine Magnesium Aluminum Silicate, Welan Gum, Xanthan Gum, Yeast Beta-Glucan, Yeast Polysaccharides, *Zea Mays* (Corn) Starch.

The present application secondly provides a kit comprising
optionally an applicator,
a container C1 comprising a dyeing composition,
a container C2a comprising a composition comprising hydrogen peroxide and
a container C2b comprising a composition comprising at least one thickener and at least one alkalinizing agent, where the dyeing composition comprises, as color-imparting component,
 (a) at least two oxidation dye precursors, where at least one oxidation dye precursor must be of the developer type or
 (b) at least two oxo dye precursors, where at least one oxo dye precursor must be a reactive carbonyl compound.

It is preferred that the nuancing agent resulting from mixing the contents of container C2a and C2b has a viscosity of from 5,000 to 100,000 mPa·s (Brookfield rotary viscometer, 25° C., spindle #4, 20 rpm).

The dyeing composition and the nuancing agent as a mixture of C2a and C2b have the preferred features as have been described in the first subject-matter of the invention. Suitable applicators are the applicators specified in the first subject-matter of the invention. Furthermore, it is preferred according to the invention to additionally include in the kit a cap with, optionally only predrawn, hole grids, and a crochet hook. The cap has the preferred features as have already been described in the first subject-matter of the invention.

The dyeing composition is preferably present in two containers C1a and C1b in the kit. If it is an oxidative dyeing composition, container C1a contains the so-called dyeing cream which comprises the dye precursors, and container 1b contains a hydrogen peroxide-containing composition.

If it is an oxo dyeing composition, the compounds of component A can be stored in container C1a and, separately, the compounds of component B can be stored in container C1b.

The invention thirdly provides the use of the kit according to the second subject-matter of the invention in a method of the first subject-matter of the invention.

EXAMPLES

The following raw materials were used in the preparation of the formulation examples below:

| | |
|---|---|
| Hydrenol ® D | $C_{16}$-$C_{18}$ fatty alcohol (INCI name: Cetearyl Alcohol) (Cognis) |
| Texapon ® NSO | sodium lauryl sulfate (INCI: Sodium Lauryl Sulfate) (Cognis) |
| Lorol ® techn. | $C_{12}$-$C_{18}$-fatty alcohol (INCI name: Coconut Alcohol) (Cognis) |
| Lorol ® C 16 | cetyl alcohol (Cognis) |
| Dehyton ® K | N,N-dimethyl-N-($C_8$-$C_{18}$-cocoamidopropyl)ammoniumacetobetaine (about 30% active substance; INCI name: Aqua (Water), Cocamidopropyl Betaine) (Cognis) |
| Aculyn ® 33 | (INCI name: Acrylates Copolymer) (Rohm & Haas) |
| Turpinal ® SL | 1-hydroxyethane-1,1-diphosphonic acid (INCI name: Etidronic Acid, Aqua (Water)) (Solutia) |
| Soda waterglass 40/42 | sodium silicate (Cognis) |
| Idranal ® III | ethylenediaminetetraacetic acid disodium salt · $2H_2O$ (INCI name: Disodium EDTA) (manufacturer: Riedel De Haen) |
| Britesil ® C20 | sodium silicate (INCI name: Sodium Silikate) (The PQ Corporation) |
| Emulgin ® B2 | cetylstearyl alcohol with about 20 EO units (INCI name: Ceteareth-20) |
| Lanette ® E | cetylstearyl alcohol sulfate sodium salt (INCI name: Sodium Cetearyl Sulfate) (Cognis) |
| Ceasit ® I | C16-18 fatty acid calcium salt (INCI name: Calcium Stearate) (Bärlocher) |
| Aerosil ® 200 | silicon dioxide (INCI name: Silica) (Degussa) |

1. Formulations of the Oxidation Hair Dyeing Composition

A dyeing cream according to TABLE 2 is prepared:

TABLE 2

Dyeing cream

| Raw material | Amount in % by wt. |
|---|---|
| Hydrenol D | 8.0 |
| Lorol techn. | 2.0 |
| Texapon NSO | 16.0 |
| Dehyton K | 10.0 |
| Ascorbic acid | 0.4 |
| Sodium sulfite | 0.5 |
| Ammonium chloride | 0.5 |
| Turpinal SL | 0.2 |
| Soda waterglass 40/42 | 0.5 |
| m-Aminophenol | 0.02 |
| Resorcinol | 0.13 |
| p-Tolylenediamine | 0.36 |
| 2,7-Dihydroxynaphthalene | 0.10 |
| 2-Methylresorcinol | 0.03 |
| 3-Amino-2-methylamino-6-methoxypyridine | 0.015 |
| 2-Amino-3-hydroxypyridine | 0.001 |
| 3-Methyl-4-aminophenol | 0.03 |
| Perfume | 0.2 |
| Ammonia (25% strength aqueous solution) | 0.6 |
| Water | ad 100 |

2. Formulations of the Nuancing Agent

The following compositions according to TABLES 3 and 4 are prepared:

TABLE 3

Nuancing Powder

| Raw material | Amount in % by wt. |
|---|---|
| Ammonium peroxydisulfate | 21.5 |
| Sodium phosphate | 4.0 |
| Aerosil 200 | 3.0 |
| Potassium persulfate | 33.0 |
| Britesil C20 | 22.0 |
| Sodium stearate | 8.0 |
| Ceasit I | 4.0 |
| Magnesium oxide | 2.0 |
| Magnesium hydroxide carbonate | 1.0 |
| Lanette E | 1.0 |
| Idranal III | 0.5 |

TABLE 4

Hydrogen peroxide solution

| Raw material | Amount in % by wt. |
|---|---|
| Lorol C16 | 3.6 |
| Eumulgin | 0.9 |
| Texapon NSO | 2.25 |
| Ammonia (25%) | 0.65 |
| Dipicolinic acid | 0.1 |
| Sodium pyrophosphate | 0.03 |
| Turpinal SL | 1.5 |
| $H_2O_2$ | 6 |
| Water | add 100 |

3. Assessment of the Dyeing Result According to Methods of the Invention 3.1 Carrying Out Steps A and B of the Method According to the Invention Shortly prior to use, a dyeing cream as in TABLE 2 was mixed with the oxidizing agent preparation according to TABLE 5 in the weight ratio 1:1.

TABLE 5

Oxidizing Agent Preparation

| Raw material | Amount in % by wt. |
|---|---|
| Hydrogen peroxide | 6.00 |
| Aculyn ® 33 | 3.40 |
| Texapon ® NSO | 2.00 |
| Turpinal SL | 1.50 |
| Sodium pyrophosphate | 0.03 |
| Dipicolinic acid | 0.10 |
| Ammonia (25% strength aqueous solution) | 0.62 |
| Water | ad 100 |

2 g of the mixture prepared above were left on 1 g of human hair tress (curling natural white) for a period of 30 minutes at 32° C. on the hair and then rinsed off. The hair tress was dried (step B of the method according to the invention) and the dyeing result was assessed.

3.2 Carrying Out Step C of the Method According to the Invention 25.0 g of the nuancing powder according to TABLE 3 is mixed with 50 ml of the composition according to Table 4 to give the nuancing agent.

Onto a fiber bundle separated from the hair tress dyed above and consisting of about one third of the hair fibers, 1 g of the nuancing agent are applied using a mascara brush uniformly over the entire area of the fiber bundle, left on the hair for a period of 10 minutes at 32° C. and then rinsed off. The hair tress was dried and the dyeing result of the nuanced hair was assessed. The hair was given a blonde coloration with pale blonde color reflections in the nuanced area.

4. Use of a Cap with Hole Grid

A hair dyeing composition was prepared by mixing the dyeing cream from TABLE 2 with the oxidizing agent preparation according to TABLE 5 in a weight ratio of 1:1.

This hair dyeing composition was applied to the entire head hair of a test subject with pale blonde starting hair and rinsed off again after a contact time of 30 minutes (step A of the method according to the invention). The hair was dried (step B of the method according to the invention) and was given a uniformly blonde coloration.

The head hair is covered with a cap having a plurality of holes arranged in a grid-like pattern and individual hair strands are pulled through the holes in the cap uniformly over the entire surface of the cap using a crochet hook. The hair strands which have been pulled through are combed.

The nuancing agent is prepared from 25.0 g of the nuancing powder according to TABLE 3 and 50 ml of the composition according to TABLE 4 by mixing and applied to the hair strands using a brush. After a contact time of 30 minutes, the nuancing agent is rinsed off and the cap is removed from the head (step C according to the invention).

The hair is washed with a standard commercial shampoo and then dried.

Hair whose basic shade is blonde and has pale blonde strands both in the covering hair and also in the areas of hair underneath is obtained. The strands are nuanced uniformly from the hair roots to the ends and form a marked contrast to the non-nuanced hair.

The invention claimed is:

1. A method for dyeing keratin-containing fibers, in particular human hair, comprising the steps of: (A) coloring the hair by contacting the hair with a dyeing composition, comprising color-imparting components for a contact time Z1; (B) rinsing the hair to remove the dying composition; (C) optionally drying the rinsed hair; (D) contacting at least a portion of the hair from step (B) or (C) with a nuancing agent having a viscosity of from 5000 to 100 000 mPa·s comprising, in a cosmetic carrier, at least one thickener, hydrogen peroxide and at least one alkalinizing agent for a contact time Z2; (E) rinsing the hair to remove the adjusting agent; wherein the dyeing composition comprises a color-imparting component comprising,
   (a) at least two oxidation dye precursors, where at least one oxidation dye precursor must be of the developer type or
   (b) at least two oxo dye precursors, where at least one oxo dye precursor must be a reactive carbonyl compound.

2. The method of claim 1 wherein the time between the end of step A and the beginning of step (D) are at most 60 minutes.

3. The method of claim 1 wherein the dyeing composition is free from direct dyes.

4. The method of claim 1 wherein the oxidation dye precursors are developer types selected from the group consisting of those formed from p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol, N,N'-bis(β-hydroxyethyl)-N,N'-bis(4'-aminophenyl)-1,3-diaminopropan-2-ol, N,N'-bis(β-hydroxyethyl)-N,Nβ-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-diethyl-N,N'-bis(4'-amino-3'-methylphenyl)ethylenediamine, bis(2-hydroxy-5-aminophenyl)methane, 1,3-bis(2,5-diaminophenoxy)propan-2-ol, N,N'-bis(4'-aminophenyl)-1,4-diazacycloheptane, N,N'-bis(2-hydroxy-5-aminobenzyl)piperazine, N-(4'-aminophenyl)-p-phenylenediamine and 1,10-bis(2',5'-diaminophenyl)-1,4,7,10-tetraoxadecane, p-phenylenediamine, p-tolylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis(β-hydroxyethyl)-p-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl,β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-β-methoxyethyl)-p-phenylenediamine and 5,8-diaminobenzo-1,4-dioxane, 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl )-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, 2,5,6-triaminopyrimidine, 2,5-diaminopyridine, 2-(4'-methoxyphenyl)amino-3-aminopyridine, 2,3-diamino-6-methoxypyridine, 2-(β-methoxyethyl)amino-3-amino-6-methoxypyridine and 3,4-diaminopyridine and physiologically compatible salts thereof.

5. The method of claim 1 wherein the oxidation dye precursors are developer types selected from the group consisting of those formed from 1-naphthol, 1,5-dihydroxynaphthalene, 2,7-dihydroxynaphthalene, 1,7-dihydroxynaphthalene, 5-amino-2-methylphenol, m-aminophenol, resorcinol, m-phenylenediamine, 1-phenyl-3-methylpyrazol-5-one, 2,4-dichloro-3-aminophenol, 1,3-bis(2,4-diaminophenoxy)propane, 2-chlororesorcinol, 4-chlororesorcinol, 2-chloro-6-methyl-3-aminophenol, 3-amino-2-methylamino-6-methoxypyridine, 2-amino-3-hydroxypyridine, 2,6-dihydroxy-3,4-dimethylpyridine, 2-methylresorcinol, 5-methylresorcinol, 2-methyl-4-chloro-5-aminophenol and the physiologically compatible salts of the abovementioned compounds.

6. The method of claim 1 wherein the reactive carbonyl component is selected from the group consisting of those formed from acetophenone, propiophenone, 2-hydroxyacetophenone, 3-hydroxyacetophenone, 4-hydroxyacetophenone, 2-hydroxypropiophenone, 3-hydroxypropiophenone, 4-hydroxypropiophenone, 2-hydroxybutyrophenone, 3-hydroxybutyrophenone, 4-hydroxybutyrophenone, 2,4-dihydroxyacetophenone, 2,5-dihydroxyacetophenone, 2,6-dihydroxyacetophenone, 2,3,4-trihydroxyacetophenone, 3,4,5-trihydroxyacetophenone, 2,4,6-trihydroxyacetophenone, 2,4,6-trimethoxyacetophenone, 3,4,5-trimethoxyacetophenone, 3,4,5-trimethoxyacetophenone diethyl ketal, 4-hydroxy-3-methoxyacetophenone, 3,5-dimethoxy-4-hydroxyacetophenone, 4-aminoacetophenone, 4-dimethylaminoacetophenone, 4-morpholinoacetophenone, 4-piperidinoacetophenone, 4-imidazolinoacetophenone, 2-hydroxy-5-bromoacetophenone, 4-hydroxy-3-nitroacetophenone, acetophenone-2-carboxylic acid, acetophenone-4-carboxylic acid, benzophenone, 4-hydroxybenzophenone, 2-aminobenzophenone, 4,4'-dihydroxybenzophenone, 2,4-dihydroxybenzophenone, 2,4,4'-trihydroxybenzophenone, 2,3,4-trihydroxybenzophenone, 2-hydroxy-1-acetonaphthone, 1-hydroxy-2-acetonaphthone, chromone, chromone-2-carboxylic acid, flavone, 3-hydroxyflavone, 3,5,7-trihydroxyflavone, 4',5,7-trihydroxyflavone, 5,6,7-trihydroxyflavone, quercetin, 1-indanone, 9-fluorenone, 3-hydroxyfluorenone, anthrone, 1,8-dihydroxyanthrone, vanillin, coniferylaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-3-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 4-hydroxy-3,5-dimethoxybenzaldehyde, 4-hydroxy-3,5-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,5-dihydroxybenzaldehyde, 2,6-dihydroxybenzaldehyde, 3,4-dihydroxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-hydroxy-2-methoxybenzaldehyde, 4-dimethylaminobenzaldehyde, 4-diethylaminobenzaldehyde, 4-dimethylamino-2-hydroxybenzaldehyde, 4-diethylamino-2-hydroxybenzaldehyde, 4-pyrrolidinobenzaldehyde, 4-morpholinobenzaldehyde, 2-morpholinobenzaldehyde, 4-piperidinobenzaldehyde, 2-methoxy-1-naphthaldehyde, 4-methoxy-1-naphthaldehyde, 2-hydroxy-1-naphthaldehyde, 2,4-dihydroxy-1-naphthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-hydroxy-1-naphthaldehyde, 4-dimethylamino-1-naphthaldehyde, 2-methoxycinnamaldehyde, 4-methoxycinnamaldehyde, 4-hydroxy-3-methoxycinnamaldehyde, 3,5-dimethoxy-4-hydroxycinnamaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 4-diphenylaminobenzaldehyde, 4-dimethylamino-2-methoxybenzaldehyde, 4-(1-imidazolyl)benzaldehyde, piperonal, 2,3,6,7-tetrahydro-1H,5H-benzo[ij]quinolizine-9-carboxaldehyde, 2,3,6,7-tetrahydro-8-hydroxy-1H,5H-benzo[ij]quinolizine-9-carboxaldehyde, N-ethylcarbazole-3-aldehyde, 2-formylmethylene-1,3,3-trimethylindoline (Fischers aldehyde or tribase aldehyde), 2-indolealdehyde, 3-indolealdehyde, 1-methylindole-3-aldehyde, 2-methylindole-3-aldehyde, 1-acetylindole-3-aldehyde, 3-acetylindole, 1-methyl-3-acetylindole, 2-(1',3',3'-trimethyl-2-indolinylidene)acetaldehyde, 1-methylpyrrole-2-aldehyde, 1-methyl-2-acetylpyrrole, 4-pyridinealdehyde, 2-pyridinealdehyde, 3-pyridinealdehyde, 4-acetylpyridine, 2-acetylpyridine, 3-acetylpyridine, pyridoxal, quinoline-3-aldehyde, quinoline-4-aldehyde, antipyrine-4-aldehyde, furfural, 5-nitrofurfural, 2-thenoyltrifluoroacetone, chromone-3-aldehyde, 3-(5'-nitro-2'-furyl)acrolein, 3-(2'-furyl)acrolein and imidazole-2-aldehyde, 1,3-diacetylbenzene, 1,4-diacetylbenzene, 1,3,5-triacetylbenzene, 2-benzoylacetophenone, 2-(4'-methoxybenzoyl)acetophenone, 2-(2'-furoyl)acetophenone, 2-(2'-pyridoyl)acetophenone and 2-(3'-pyridoyl)acetophenone, benzylideneacetone, 4-hydroxybenzylideneacetone, 2-hydroxybenzylideneacetone, 4-methoxybenzylideneacetone, 4-hydroxy-3-methoxybenzylideneacetone, 4-dimethylaminobenzylideneacetone, 3,4-methylenedioxybenzylideneacetone, 4-pyrrolidinobenzylideneacetone, 4-piperidinobenzylideneacetone, 4-morpholinobenzylideneacetone, 4-diethylaminobenzylideneacetone, 3-benzylidene-2,4-pentanedione, 3-(4'-hydroxybenzylidene)-2,4-pentanedione, 3-(4'-dimethylaminobenzylidene)-2,4-pentanedione, 2-benzylidenecyclohexanone, 2-(4'-hydroxybenzylidene)cyclohexanone, 2-(4'-dimethylaminobenzylidene)cyclohexanone, 2-benzylidene-1,3-cyclohexanedione, 2-(4'-hydroxybenzylidene)-1,3-cyclohexanedione, 3-(4'-dimethylaminobenzylidene)-1,3-cyclohexanedione, 2-benzylidene-5,5-dimethyl-1,3-cyclohexanedione, 2-(4'-hydroxybenzylidene)-5,5-dimethyl-1,3-cyclohexanedione, 2-(4'-hydroxy-3-methoxybenzylidene)-5,5-dimethyl-1,3-cyclohexanedione, 2-(4'-dimethylaminobenzylidene)-5,5-dimethyl-1,3-cyclohexanedione, 2-benzylidenecyclopentanone, 2'-(4-hydroxybenzylidene)cyclopentanone, 2-(4'-dimethylaminobenzylidene)cyclopentanone, 5-(4-dimethylaminophenyl)penta-2,4-dienal, 5-(4-diethylaminophenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal, 5-(4-morpholinophenyl)penta-2,4-dienal, 5-(4-pyrrolidinophenyl)penta-2,4-dienal, 6-(4-dimethylaminophenyl)hexa-3,5-dien-2-one, 6-(4-diethylaminophenyl)hexa-3,5-dien-2-one, 6-(4-methoxyphenyl)hexa-3,5-dien-2-one, 6-(3,4-dimethoxyphenyl)hexa-3,5-dien-2-one, 6-(2,4-dimethoxyphenyl)hexa-3,5-dien-2-one, 6-(4-piperidinophenyl)hexa-3,5-dien-2-one, 6-(4-morpholinophenyl)hexa-3,5-dien-2-one, 6-(4-pyrrolidinophenyl)hexa-3,5-dien-2-one, 5-(4-dimethylamino-1-naphthyl)penta-3,5-dienal, 2-nitrobenzaldehyde, 3-nitrobenzaldehyde, 4-nitrobenzaldehyde, 4-methyl-3-nitrobenzaldehyde, 3-hydroxy-4-nitrobenzaldehyde, 4-hydroxy-3-nitrobenzaldehyde, 5-hydroxy-2-nitrobenzaldehyde, 2-hydroxy-5-nitrobenzaldehyde, 2-hydroxy-3-nitrobenzaldehyde, 2-fluoro-3-nitrobenzaldehyde, 3-methoxy-2-nitrobenzaldehyde, 4-chloro-3-nitrobenzaldehyde, 2-chloro-6-nitrobenzaldehyde, 5-chloro-2-nitrobenzaldehyde, 4-chloro-2-nitrobenzaldehyde, 2,4-dinitrobenzaldehyde, 2,6-dinitrobenzaldehyde, 2-hydroxy-3-methoxy-5-nitrobenzaldehyde, 4,5-dimethoxy-2-nitrobenzaldehyde, 6-nitropiperonal, 2-nitropiperonal, 5-nitrovanillin, 2,5-dinitrosalicylaldehyde, 5-bromo-3-nitrosalicylaldehyde, 3-nitro-4-formylbenzenesulfonic acid, 4-nitro-1-naphthaldehyde, 2-nitrocinnamaldehyde, 3-nitrocinnamaldehyde, 4-nitrocinnamaldehyde, 9-methyl-3-carbazolealdehyde, 9-ethyl-3-carbazolealdehyde, 3-acetylcarbazole, 3,6-diacetyl-9-ethylcarbazole, 3-acetyl-9-methylcarbazole, 1,4-dimethyl-3-carbazolealdehyde, 1,4,9-trimethyl-3-carbazolealdehyde, 4-formyl-1-methylpyridinium-, 2-formyl-1-methylpyridinium-, 4-formyl-1-ethylpyridinium-, 2-formyl-1-ethylpyridinium-, 4-formyl-1-benzylpyridinium-, 2-formyl-1-benzylpyridinium-, 4-formyl-1,2-dimethylpyridinium-4-formyl-1,3-dimethylpyridinium-, 4-formyl-1-methylquinolinium-, 2-formyl-1-methylquinolinium-, 4-acetyl-1-methylpyridinium-, 2-acetyl-1-methylpyridinium-, 4-acetyl-1-methylquinolinium-, 5-formyl-1-methylquinolinium-, 6-formyl-1-methylquinolinium-, 7-formyl-1-methylquinolinium-, 8-formyl-1-methylquinolinium, 5-formyl-1-ethylquinolinium-, 6-formyl-1-ethylquinolinium-, 7-formyl-1-ethylquinolinium-, 8-formyl-1-ethylquinolinium, 5-formyl-1-benzylquinolinium-, 6-formyl-1-benzylquinolinium-, 7-formyl-1-benzylquinolinium-, 8-formyl-1-benzylquinolinium, 5-formyl-1-allylquinolinium-, 6-formyl-1-allylquinolinium-, 7-formyl-1-allylquinolinium- and 8-formyl-1-allylquinolinium-, 5-acetyl-1-methylquinolinium-,6-acetyl-1-methylquinolinium-, 7-acetyl-1-methylquinolinium-, 8-acetyl-1-methylquinolinium-, 5-acetyl-1-ethylquinolinium-, 6-acetyl-1-ethylquinolinium-, 7-acetyl-1-ethylquinolinium-, 8-acetyl-1-ethylquinolinium-, 5-acetyl-1-benzylquinolinium-, 6-acetyl-1-benzylquinolinium-, 7-acetyl-1-benzylquinolinium-, 8-acetyl-1-benzylquinolinium-, 5-acetyl-1-allylquinolinium-, 6-acetyl-1-allylquinolinium-, 7-acetyl-1-allylquinolinium- and 8-acetyl-1-allylquinolinium-, 9-formyl-10-methylacridinium-, 4-(2'-formylvinyl)-1-methylpyridinium-, 1,3-dimethyl-2-(4'-formylphenyl)benzimidazolium-, 1,3-dimethyl-2-(4'-formylphenyl)imidazolium-, 2-(4'-formylphenyl)-3-methylbenzothiazolium-, 2-(4'-acetylphenyl)-3-methylbenzothiazolium-, 2-(4'-formylphenyl)-3-methylbenzoxazolium-, 2-(5'-formyl-2'-furyl)-3-methylbenzothiazolium-, 2-(5'-formyl-2'-furyl)-3- methylbenzothiazolium-, 2-(5'-formyl-2'-thienyl)-3-methylbenzothiazolium-, 2-(3'-formylphenyl)-3-methylbenzothiazolium-, 2-(4'-formyl-1-naphthyl)-3-methylbenzothiazolium-, 5-chloro-2-(4'-formylphenyl)-3-methylbenzothiazolium-, 2-(4'-formylphenyl)-3,5-dimethylbenzothiazolium benzenesulfonate, p-toluenesulfonate, methanesulfonate, perchlorate, sulfate, chloride, bromide, iodide, tetrachlorozincate, methylsulfate, trifluoromethanesulfonate, tetrafluoroborate, isatin, 1-methylisatin, 1-allylisatin, 1-hydroxymethylisatin, 5-chloroisatin, 5-methoxyisatin, 5-nitroisatin, 6-nitroisatin, 5-sulfoisatin, 5-carboxyisatin, quinisatin, 1-methylquinisatin, and any mixtures of the above compounds.

7. The method of claim 1 wherein the nuancing agent is further comprised of at least one peroxo compound.

8. The method of claim 1 wherein the nuancing agent is applied to part of the previously dyed keratin-containing fibers by means of a brush or an applicette.

9. A method for dyeing keratin-containing fibers in a head of human hair comprising the steps of: (A) coloring the hair by contacting the hair with a dyeing composition comprising color-imparting components for a contact time Z1; (B) rinsing the hair to remove the dying composition; (C) optionally drying the rinsed hair; (D) placing a cap over the head wherein the cap has a plurality of markings for the placement of holes in the surface of the cap arranged in a grid-like pattern spread over the surface of the cap; (E) pulling a portion of the fibers through the holes; (F) contacting the portion of the hair from step (E) with a nuancing agent having a viscosity of from 5000 to 100 000 mPa·s comprising, in a cosmetic carrier, at least one thickener, hydrogen peroxide and at least one alkalinizing agent for a contact time Z2; (G) removing the cap and rinsing the hair to remove the adjusting agent; wherein the dyeing composition comprises a color-imparting component comprising,
  (a) at least two oxidation dye precursors, where at least one oxidation dye precursor must be of the developer type or
  (b) at least two oxo dye precursors, where at least one oxo dye precursor must be a reactive carbonyl compound.

10. The method of claim 9 wherein the cap has a plurality of pre-formed holes in the surface of the cap arranged in a grid-like pattern spread over the surface of the cap.

11. A kit comprising
  optionally an applicator,
  a container C1 comprising a dyeing composition,
  a container C2a comprising a composition comprising hydrogen peroxide and
  a container C2b comprising a composition comprising at least one thickener and at least one alkalinizing agent,
where the dyeing composition comprises, as color-imparting component,
  (a) at least two oxidation dye precursors, where at least one oxidation dye precursor must be of the developer type or
  (b) at least two oxo dye precursors, where at least one oxo dye precursor must be a reactive carbonyl compound, wherein the nuancing agent resulting from mixing the contents of container C2a and C2b has a viscosity of from 5000 to 100 000 mPa·s.

12. The kit of claim 11 wherein the oxidation dye precursors in a container C1a and a hydrogen peroxide-containing composition in container C1b are formulated separately.

13. A method for dyeing keratin-containing fibers, in particular human hair, comprising contacting the fibers with the contents of the kit of claim 11.

* * * * *